(12) United States Patent
Ekker et al.

(10) Patent No.: US 7,713,925 B2
(45) Date of Patent: May 11, 2010

(54) SYNDECANS AND ANGIOGENESIS

(75) Inventors: Stephen C. Ekker, St. Paul, MN (US); Eleanor Y. Chen, Jamaica Plain, MA (US)

(73) Assignee: Regents of the University of Minnesota, Saint Paul, MN (US)

( * ) Notice: Subject to any disclaimer, the term of this patent is extended or adjusted under 35 U.S.C. 154(b) by 632 days.

(21) Appl. No.: 11/537,804

(22) Filed: Oct. 2, 2006

(65) Prior Publication Data
US 2009/0005295 A1 Jan. 1, 2009

Related U.S. Application Data

(63) Continuation of application No. 10/866,589, filed on Jun. 10, 2004, now abandoned.

(51) Int. Cl.
C07K 14/00 (2006.01)
(52) U.S. Cl. .......................................... 514/2; 530/350
(58) Field of Classification Search ....................... None
See application file for complete search history.

(56) References Cited

U.S. PATENT DOCUMENTS

| | | | |
|---|---|---|---|
| 4,704,692 A | 11/1987 | Ladner | |
| 4,946,778 A | 8/1990 | Ladner et al. | |
| 5,142,047 A | 8/1992 | Summerton et al. | |
| 5,185,444 A | 2/1993 | Summerton et al. | |
| 6,242,481 B1 | 6/2001 | Udagawa et al. | |
| 6,245,512 B1 | 6/2001 | Williams et al. | |
| 6,248,586 B1 | 6/2001 | Monia et al. | |
| 6,248,724 B1 | 6/2001 | Moore et al. | |
| 2002/0048585 A1 | 4/2002 | Goetinck | |

FOREIGN PATENT DOCUMENTS

| | | |
|---|---|---|
| WO | WO 02/04028 | 1/2002 |
| WO | WO 03/004610 | 1/2003 |

OTHER PUBLICATIONS

Chen et al. Jul. 15, 2003; A morphant screen identifies an essential role for syndecan-2 in vascular development. Developmental Biology 259(2): 538.*
Wu et al. 2000; EMBL AF262048.*
Chen et al. 2002; EMBL AY091914.*
GenBank Accession No. AI558535 dated Jun. 7, 2001, 2 pages.
GenBank Accession No. AI959303 dated Jun. 7, 2001, 2 pages.
GenBank Accession No. AK027720 dated Sep. 12, 2006, 3 pages.
GenBank Accession No. XM_040582 dated Jan. 4, 2003, 3 pages.
Ahn et al., "Cloning of the putative tumour suppressor gene for hereditary multiple exostoses (EXT1)," *Nature Genetics*, 1995, 11:137-143.
Bernfield et al., "Functions of cell surface heparan sulfate proteoglycans," *Annu. Rev. Biochem.*, 1999, 68:729-777.
Better et al., "*Escherichia coli* secretion of an active chimeric antibody fragment," *Science*, 1988, 240:1041-1043.

Birch and Skerry, "Differential Regulation of Syndecan Expression by Osteosarcoma Cell Lines in Response to Cytokines but Not Osteotropic Hormones," *Bone*, 1999, 24(6):571-578.
Bissell and Radisky, "Putting Tumors in Context," *Nature*, 2001, 1:46-54.
Boyle et al., "DNA immunization: Induction of higher avidity antibody and effect of route on T cell cytotoxicity," *Proc. Natl. Acad. Sci. USA*, 1997, 94:14626-14631.
Braasch and Corey, "Locked nucleic acid (LNA): fine-tuning the recognition of DNA and RNA," *Chemistry & Biology*, 2001, 8:1-7.
Brown et al., "Insights into early vasculogenesis revealed by expression of the ETS-domain transcription factor Fli-1 in wild-type and mutant zebrafish embryos," *Mech. Dev.*, 2000, 90:237-252.
Bullock et al., "Renal agenesis in mice homozygous for a gene trap mutation in the gene encoding heparan sulfate 2-sulfotransferase," *Genes Dev.*, 1998, 12:1894-1906.
Carey, "Syndecans: multifunctional cell-surface co-receptors," *Biochem. J.*, 1997, 327:1-16.
Carmeliet and Collen, "Molecular analysis of blood vessel formation and disease," *Am. J. Physiol.*, 1997, 273(5, Part 2):H2091-H2104.
Carmeliet and Jain, "Angiogenesis in cancer and other diseases," *Nature*, 2000, 407:249-257.
Carmeliet et al., "Abnormal blood vessel development and lethality in embryos lacking a single VEGF allele," *Nature*, 1996, 380:435-439.
Chan et al., "Dissection of angiogenic signaling in zebrafish using a chemical genetic approach," *Cancer Cell*, 2002, 1:257-267.
Chen et al., "Molecular characterization of chicken syndecan-2 proteoglycan," *Biochem. J.*, 2002, 366:481-490.
Chen et al., "Syndecan-2 is essential for angiogenic sprouting during zebrafish development," *Blood*, 2004, 103:1710-1719.
Chowdhury et al., "Generation of high titer antisera in rabbits by DNA immunization," *J. Immunol. Meth.*, 2001, 249:147-154.
Clark et al., "An Oligonucleotide Fingerprint Normalized and Expressed Sequence Tag Characterized Zebrafish cDNA Library," *Genome Res.*, 2001, 11:1594-1602.
Clasper et al., "Inducible Expression of the Cell Surface Heparan Sulfate Proteoglycan Syndecan-2 (Fibroglycan) on Human Activated Macrophages Can Regulate Fibroblast Growth Factor Action," *J. Biol. Chem.*, 1999, 274(34):24113-24123.
Cleaver and Krieg, "VEGF mediates angioblast migration during development of the dorsal aorta," *Development*, 1998, 125:3905-3914.
Cole et al., "The EBV-Hybridoma Technique and Its Application to Human Lung Cancer," *Monoclonal Antibodies and Cancer Therapy*, 1985, Alan R. Liss, Inc., pp. 77-96.
Contreras et al., "Syndecan-2 expression in colorectal cancer-derived HT-29 epithelial cells induces a migratory phenotype," *Bio. Biophysic. Res. Chem.*, 2001, 286:742-751.

(Continued)

*Primary Examiner*—Karen Cochrane Carlson
(74) *Attorney, Agent, or Firm*—Fish & Richardson P.C.

(57) ABSTRACT

The invention provides methods and materials related to modulating syndecan levels and angiogenesis in an animal. The invention provides syndecan polypeptides and nucleic acids encoding syndecan polypeptides, including dominant negative syndecan polypeptides. The invention also provides polynucleotides and polynucleotide analogues for modulating angiogenesis, as well as cells and embryos containing the polynucleotides and polynucleotide analogues. The invention further provides methods for identifying syndecan- and angiogenesis-modulating agents.

3 Claims, 17 Drawing Sheets

OTHER PUBLICATIONS

Cook, "Chapter 2: Antisense Medicinal Chemistry," *Antisense Research and Application*, 1998, Springer-Verlag, Germany, pp. 51-101.

Cote et al., "Generation of human monoclonal antibodies reactive with cellular antigens," *Proc. Natl. Acad. Sci. USA*, 1983, 80:2026-2030.

Couchman et al., "Syndecans and Cell Adhesion," *International Review of Cytology: A Survey of Cell Biology*, 2001, Academic Press, 207:113-150.

Crystal, "Transfer of Genes to Humans: Early Lessons and Obstacles to Success," *Science*, 1995, 270:404-410.

Cui et al., "Inhibition of skiA and skiB gene expression ventralizes zebrafish embryos," *Genesis*, 2001, 30:149-153.

Darnell et al., "Chapter 2: Molecules in Cells," *Molecular Cell Biology*, Second Edition, 1990, Scientific American Books, Inc., pp. 43-84.

David et al., "Spatial and temporal changes in the expression of fibroglycan (syndecan-2) during mouse embryonic development," *Development*, 1993, 119:841-854.

Deonarain, "Ligand-targeted receptor-mediated vectors for gene delivery," *Exp. Opin. Ther. Patients*, 1998, 8(1):53-69.

Detrich III et al., "Intraembryonic hematopoietic cell migration during vertebrate development," *Proc. Natl. Acad. Sci. USA*, 1995, 92:10713-10717.

Dobra et al., "Differentiation of Mesothelioma Cells Is Influenced by the Expression of Proteoglycans," *Exp. Cell Res.*, 2000, 258:12-22.

Echtermeyer et al., "Delayed wound repair and impaired angiogenesis in mice lacking syndecan-4," *J. Clin. Invest.*, 2001, 107:R9-R14.

Ekker and Larson, "Morphant Technology in Model Development Systems," *Genesis*, 2001, 30:89-93.

Ekker et al., "Patterning activities of vertebrate hedgehog proeteins in the developing eye and brain," *Curr. Biol.*, 1995, 5:944-955.

Ekker, "Morphants: a new systematic vertebrate functional genomics approach," *Yeast*, 2000, 17:302-306.

Elenius and Jalkanen, "Function of the syndecans—a family of cell surface proteoglycans," *J. Cell Science*, 1994, 107:2975-2982.

Eriksson and Löfberg, "Development of the Hypochord and Dorsal Aorta in the Zebrafish Embryo (Danio rerio)," *J. Morphology*, 2000, 244:167-176.

Essner et al., "Syndecan-2," *Int. J. Biochem. Cell Biol.*, 2006, 38:152-156.

Ferrara et al., "Heterozygous embryonic lethality induced by targeted inactivation of the VEGF gene," *Nature*, 1996, 380:439-442.

Ferrara, "Molecular and biological properties of vascular endothelial growth factor," *Mol. Med.*, 1999, 77:527-543.

Flohe and Schwabe, "Kinetics of Purified Catechol O-Methyltransferase," *Biochim. Biophys. Acta*, 1970, 220:469-476.

Folkman and D'Amore, "Blood Vessel Formation: What Is Its Molecular Basis?" *Cell*, 1996, 87:1153-1155.

Fouquet et al., "Vessel Patterning in the Embryo of the Zebrafish: Guidance by Notochord," *Dev. Biol.*, 1997, 183:37-48.

Froehler et al., "Phosphoramidate analogues of DNA: synthesis and thermal stability of heteroduplexes," *Nucl. Acids Res.*, 1988, 16(11):4831-4839.

Gering et al., "The SCL gene specifies haemangioblast development from early mesoderm," *EMBO J.*, 1998, 17(14):4029-4045.

Gibbs and Schmale, "GFP as a Genetic Marker Scorable Throughout the Life Cycle of Transgenic Zebra Fish," *Marine Biotechnol.*, 2000, 2:107-125.

Godbey and Mikos, "Recent Progress in gene delivery using non-viral transfer complexes," *J. Controlled Release*, 2001, 72:115-125.

Habuchi et al., "Molecular Characterization and Expression of Heparan-sulfate 6-Sulfotransferase," *J. Biol. Chem.*, 1998, 273(15):9208-9213.

Habuchi et al., "The Occurrence of Three Isoforms of Heparan Sulfate 6-O-Sulfotransferase Having Different Specificities for Hexuronic Acid Adjacent to the Targeted N-Sulfoglucosamine," *J. Biol. Chem.*, 2000, 275(4):2859-2868.

Hamers et al., "Severe mental retardation in a patient with tricho-rhino-phalangeal syndrome type I and 8q deletion," *Eur. J. Pediatr.*, 1990, 149:618-620.

Hou et al., "A 4-Megabase YAC Contig That Spans the Langer-Giedion Syndrome Region on Human Chromosome 8q24.1: Use in Refining the Location of the Trichorhinophalangeal Syndrome and Multipe Exostoses Genes (TRPS1 and EXT1)," *Genomics*, 1995, 29:87-97.

Hukriede et al., "Radiation hybrid mapping of the zebrafish genome," *Proc. Natl. Acad. Sci. USA*, 1999, 96:9745-9750.

Huse et al., "Generation of a Large Combinatorial Library of the Immunoglobulin Repertoire in Phage Lambda," *Science*, 1989, 246:1275-1281.

Hyatt and Ekker, "Chapter 8: Vectors and Techniques for Ectopic Gene Expression," *Methods in Cell Biology*, vol. 59, 1999, Academic Press, San Diego, CA, pp. 117-126.

Isogai et al., "The Vascular Anatomy of the Developing Zebrafish: An Atlas of Embryonic and Early Larval Development," *Dev. Biol.*, 2001, 230:278-301.

Jones et al., "Replacing the complementarity-determining regions in a human antibody with those from a mouse," *Nature*, 1986, 321:522-525.

Jowett et al., "Chapter 6: Analysis of Protein and Gene Expression," *Methods Cell Biol.*, 1999, 59:63-85.

Klass et al., "Control of extracellular matrix assembly by syndecan-2 proteoglycan," *J. Cell Science*, 2000, 113:493-506.

Klee et al., "Target Selection for Danio rerio Functional Genomics," *Genesis*, 2001, 30:123-125.

Köhler and Milstein, "Continuous cultures of fused cells secreting antibody of predefined specificity," *Nature*, 1975, 256:495-497.

Kozbor and Roder, "The production of monoclonal antibodies from human lymphocytes," *Immunol. Today*, 1983, 4(3):72-79.

Kramer and Yost, "Ectodermal Syndecan-2 Mediates Left-Right Axis Formation in Migrating Mesoderm as a Cell-Nonautonomous Vg1 Cofactor," *Developmental Cell*, 2002, 2:115-124.

Kusano et al., "Participation of Syndecan 2 in the Induction of Stress Fiber Formation in Cooperation with Integrin $\alpha 5\beta 1$: Structural Characteristics of Heparan Sulfate Chains with Avidity to COOH-Terminal Heparin-Binding Domain of Fibronectin," *Exp. Cell Res.*, 2000, 256:434-444.

Laham et al., "Gene transfer to induce angiogenesis in myocardial and limb ischaemia," *Expert Opin. Biol. Ther.*, 2001, 1(6):985-994.

Langford et al., "Multiple heparan sulfate chains are required for optimal syndecan-1 function," 1998, *J. Biol. Chem.*, 273(45):29965-29971.

Liao et al., "The zebrafish gene cloche acts upstream of a flk-1 homologue to regulate endothelial cell differentiation," *Development*, 1997, 124:381-389.

Miller and Vile, "Targeted vectors for gene therapy," *FASEB J.*, 1995, 9:190-9.

Miller et al., "Nonionic Nucleic Acid Analogues. Synthesis and Characterization of Dideoxyribonucleoside Methylphosphonates," *Biochemistry*, 1979, 18(23):5134-5143.

Miller et al., "Oligothymidylate Analogues Having Stereoregular, Alternating Methylphosphonate/Phosphodiester Backbones," *J. Biol. Chem.*, 1980, 255(20):9659-9665.

Modrowski et al., "Syndecan-2 Is Involved in the Mitogenic Activity and Signaling of Granulocyte-Macrophage Colony-stimulating Factor in Osteoblasts," *J. Biol. Chem.*, 2000, 275(13):9178-9185.

Momeni et al., "Mutations in a new gene, encoding a zinc-finger protein, cause tricho-rhino-phalangeal syndrome type I," *Nature Genetics*, 2000, 24:71-74.

Munesue et al., "The role of syndecan-2 in regulation of actin-cytoskeletal organization of Lewis lung carcinoma-derived metastatic clones," *Biochem. J.*, 2002, 363:201-209.

Nasevicius and Ekker, "Effective targeted gene 'knockdown' in zebrafish," *Nature Genetics*, 2000, 26:216-220.

Nasevicius and Ekker, "The zebrafish is a novel system for functional genomics and therapeutic development applications," *Curr. Opin. Mol. Ther.*, 2001, 3:224-228.

Nasevicius et al., "Distinct requirements for zebrafish angiogenesis revealed by a VEGF-A morphant," *Yeast*, 2000, 17:294-301.

Nasevicius et al., "Evidence for a frizzled-mediated wnt pathway required for zebrafish dorsal mesoderm formation," *Development*, 1998, 125:4283-4292.

Nasevicius et al., "Sequence, expression, and location of Zebrafish frizzled 10," *Mech. Dev.*, 2000, 92:311-314.

Negishi et al., "Structure and Function of Sulfotransferases," *Arch. Biochem. Biophys.*, 2001, 390(2):149-157.

Nielsen et al., "Sequence-Selective Recognition of DNA by Strand Displacement with a Thymine-Substituted Polyamide," *Science*, 1991, 254:1497-1500.

Nugent and Iozzo, "Fibroblast growth factor-2," *Int. J. Biochem. Cell Biol.*, 2000, 32:115-120.

Park et al., "Syndecan-2 Mediates Adhesion and Proliferation of Colon Carcinoma Cells," *J. Biol. Chem.*, 2002, 277(33):29730-29736.

Pitha and Pitha, "Preparation and Properties of Poly-9-vinyladenine," *Biopolymers*, 1970, 9:965-977.

Pitha et al., "Poly(I-Vinyluracil): The Preparation and Interactions with Adenosine Derivatives," *Biochim. Biophys. Acta*, 1970, 204:39-48.

Pouton and Seymour, "Key issues in non-viral gene delivery," *Adv. Drug Deliv. Rev.*, 2001, 187-203.

Puri et al., "The receptor tyrosine kinase TIE is required for integrity and survival of vascular endothelial cells," *EMBO J.*, 1995, 14(23):5884-5891.

Rapraeger, "Molecular interactions of syndecans during development," *Seminars in Cell & Developmental Biology*, 2001, 12:107-116.

Read et al., "Barriers to Gene Delivery Using Synthetic Vectors," *Adv. Genomics*, 2005, 53:20-46.

Roman and Weinstein, "Building the vertebrate vasculature: research is going swimmingly," *BioEssays*, 2000, 22:882-893.

Romano et al., "Gene Transfer Technology in Therapy: Current Applications and Future Goals," *Stem Cells*, 1999, 17:191-202.

Roskams et al., "Heparan Sulphate Proteoglycan Expression in Human Primary Liver Tumours," *J. Pathol.*, 1998, 185:290-297.

Rupp et al., "Xenopus embryos regulate the nuclear localization of XM yoD," *Genes Dev.*, 1994, 8:1311-1323.

Salmivirta and Jalkanen, "Syndecan family of cell surface proteoglycans: developmentally regulated receptors for extracellular effector molecules," *Experientia*, 1995, 51(9-10):863-72.

Schulte-Merker et al., "The protein product of the zebrafish homologue of the mouse T gene is expressed in nuclei of the germ ring and the notochord of the early embryo," *Development*, 1992, 116:1021-1032.

Sumanas et al., "Zebrafish frizzled-2 morphant displays defects in body axis elongation," *Genesis*, 2001, 30:114-118.

Summerton and Weller, "Morpholino Antisense Oligomers: Design, Preparation, and Properties," *Antisense & Nucleic Acid Drug Development*, 1997, 7:187-195.

Tilgmann and Kalkkinen, "Purification and partial characterization of rat liver soluble catechol-O-methyltransferase," *FEBS Lett.*, 1990, 264(1):95-99.

Tomayko and Reynolds, "Determination of subcutaneous tumor size in athymic (nude) mice," *Cancer Chemother. Pharmacol.*, 1989, 24:148-154.

Toyoda et al., "Structural Analysis of Glycosaminoglycans in Animals Bearing Mutations in sugarless, sulfateless, and tout-velu," *J. Biol. Chem.*, 2000, 275(29):21856-21861.

Turner and Weintraub, "Expression of achaete-scute homolog 3 in Xenopus embryos converts ectodermal cells to a neural fate," *Genes Dev.*, 1994, 8:1434-1447.

Verma and Somla, "Gene therapy-promises, problems and prospects," *Nature*, 1997, 389:239-242.

Vermeulen et al., "Quantification of angiogenesis in solid human tumours: an international consensus on the methodology and criteria of evaluation," *Eur. J. Cancer*, 1996, 32A:2474-2484.

Wang et al., "Molecular Distinction and Angiogenic Interaction between Embryonic Arteries and Veins Revealed by ephrin-B2 and Its Receptor Eph-B4," *Cell*, 1998, 93:741-753.

Wilkinson, "Chapter 6: Whole mount in situ hybridization of vertebrate embryos," *In Situ Hybridation: A Practical Approach*, vol. 109, 1992, IRL Press, pp. 75-83.

Williams and Fuki, "Cell-surface heparan sulfate proteoglycans: dynamic molecules mediating ligand catabolism," *Curr. Opin. Lipidology*, 1997, 8(5):253-62.

Woods, "Syndecans: transmembrane modulators of adhesion and matrix assembly," *J. Clin. Invest.*, 2001, 107(8):935-941.

Yancopoulos et al., "Vascular-specific growth factors and blood vessel formation," *Nature*, 2000, 407:242-248.

Yancopoulos et al., "Vasculogenesis, Angiogenesis, and Growth Factors: Ephrins Enter the Fray at the Border," *Cell*, 1998, 93:661-664.

Zimmermann, "The syndecans, tuners of transmembrane signaling," *FASEB J.*, 1999, Suppl:S91-S100.

* cited by examiner

Figure 1 ccacgcgtccgcccacgcgtccgagacgcgatttccgctttcacgagcgaagactgagg 60
aattatgaggaacctttggatgattttaaccctcggcttgactgcctttctctccgggga 120
gcggatatcagtgtctgcggccaaatctcccacgacagatgacctgtacctggagga 180
ggctggatctggaggatacctgaagatgatgatcagtaaacacactgttcttcgtgcctaaagc 240
agccggagaggttattgaagatcccgtcacagacttcacaccgaaagtggagacagtgactcaca 300
agagcccacgcgcaggactccaccaaagactcacaccgaaagtggagacagtgactcaca 360
agacgccccaaagactcgaagaaaacgcaggatagaggttgcagtcccgtcacagaaga 420
ctctcgcagaaacccctgtcaccagcatccgacctcccatggatccccca 480
agacgtccagtcgatcagaaatcttttcgccatctttcctcctgctgttgattgcagg 540
aggagtgatcggcttcctcttcgccatctttcctcctgctggtttaccgcatgag 600
aaagaggacgagggcagctacgatctgggagagaggaaaaccgtccggagcggggcctatca 660
gaaagctcccaccaaggagttttacgcataa 691

SEQ ID NO:1

Figure 2

```
MRNLWMILTLGLTAFLSGERISVSAAKSPSTTDDLYLEEAGSGGYPEDDDFSSGSGSGA    60
GEVIEDPVTVNTLFFVPKAEPTQDSTKDFTPKVETVTSQDAPKDSKKRRIEVAVPVTEDS  120
RRNPVTSTTSIPRPPMDPQDVQSENLFQRTEVLAAVIAGGVIGFLFAIFLILLVYRMRK   180
KDEGSYDLGERKPSGAAYQKAPTKEFYA                                  209
```

SEQ ID NO:2

Figure 3

```
mSyndecan2   MQRAWILLTL GLMACVSAE- ---------- ----TRTELT SDKDMYLDNS SIEEASGVYP IDDDDYSSAS    55
rSyndecan-2  MQRAWILLTL GLMACVSAE- ---------- ----TRAELT SDKDMYLDSS SIEEASGLYP IDDDDYSSAS    55
hSyndecan2   MRRAWILLTL GLVACVSAE- ---------- ----SRAELT SDKDMYLDNS SIEEASGVYP IDDDDYASAS    55
Xsyndecan-2  MRNVWLIVPF ALLAAFSGE- ---------- ------TWAQ ADRDLYIDST ---ESSGNYP VDDDDYSSGS    50
zSyndecan-2  MRNLWMLTTL GLTAFLSGER ISVSAAKSPS TTDDLYLEEA ---------- -----GSGGYP EDDDDFSSGS   56 mSyndecan2   GSGADEDIES PV-----L-TT SQLIPRIPLI SASSPKVETM TLKTQSITPA QTESPEETDK   110
rSyndecan-2  GSGAYEDKGS PD-----L-TT SQLIPRISLI SAA-PEVETM TLKTQSITPT QTESPEETDK   109
hSyndecan2   GSGADEDVES PE-----L-TT SRPLPKILLT SAA-PKVETT TLNIQNKIPA QTKSPEETDK   109
Xsyndecan-2  GSGIPAHDDD EDNV-VLTTV QTLISSPSSE MPY----VDTT TLKTQTKMAP ETKEPGEV-    104
zSyndecan-2  GSGAGEVIED PVTVNTLFFV PKAEPTQDST KDFTPKVETV TSQDAPKDSK KRRIEVAVPV   116 mSyndecan2   EEVDISEAEE KLGPAIKSTD VYTEKHSDNL FKRTEVLAAV IAGGVIGFLF AIFLILLLVY   170
rSyndecan-2  KEFEISEAEE KQDPAVKSTD VYTEKHSDNL FKRTEVLAAV IAGGVIGFLF AIFLILLLVY   169
hSyndecan2   EKVHLSDSER KMDPAEEDTN VYTEKHSDSL FKRTEVLAAV IAGGVIGFLF AIFLILLLVY   169
Xsyndecan-2  -ESTNTVLVH ENKNIIQTA- ----THTENL FHRTEVLAAV IAGGGIGFLF AVFLILLLVY   158
zSyndecan-2  TEDSRRNPVT STTSIPRPPM DPQDVQSENL FQRTEVLAAV IAGGVIGFLF AIFLILLLVY   176 mSyndecan2   RMRKKDEGSY DLGERKPSSA AYQKAPTKEF YA  202  (SEQ ID NO:3)
rSyndecan-2  RMRKKDEGSY DLGERKPSSA AYQKAPTKEF YA  201  (SEQ ID NO:4)
hSyndecan2   RMRKKDEGSY DLGERKPSSA AYQKAPTKEF YA  201  (SEQ ID NO:5)
Xsyndecan-2  RMRKKDEGSY DLGERKPSSA VYQKAPTKEF YA  190  (SEQ ID NO:6)
zSyndecan-2  RMRKKDEGSY DLGERKPSGA AYQKAPTKEF YA  208  (SEQ ID NO:2)
```

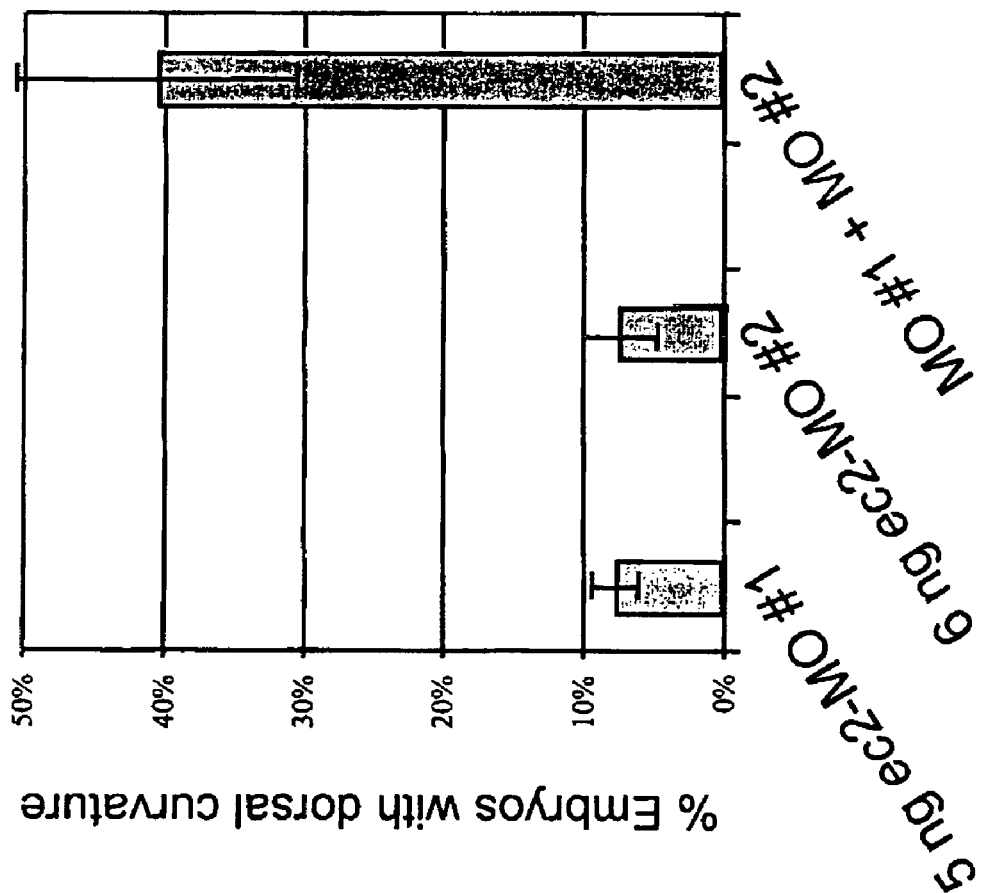

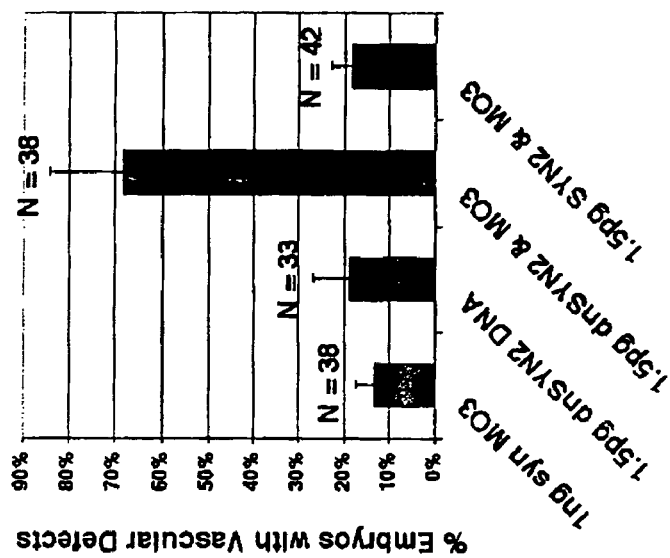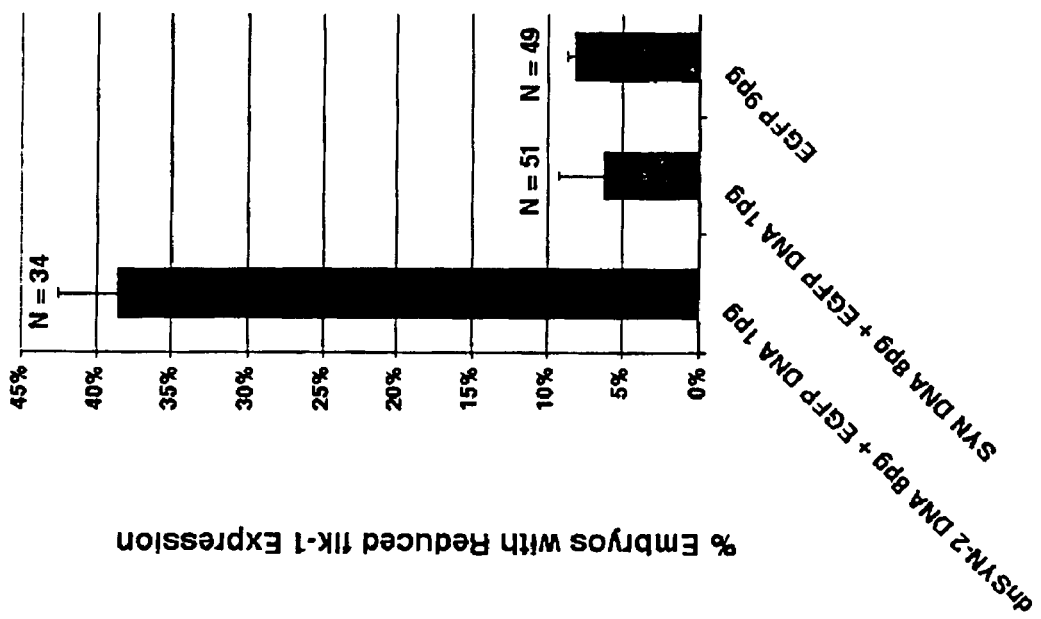
Figure 10A
Figure 10B

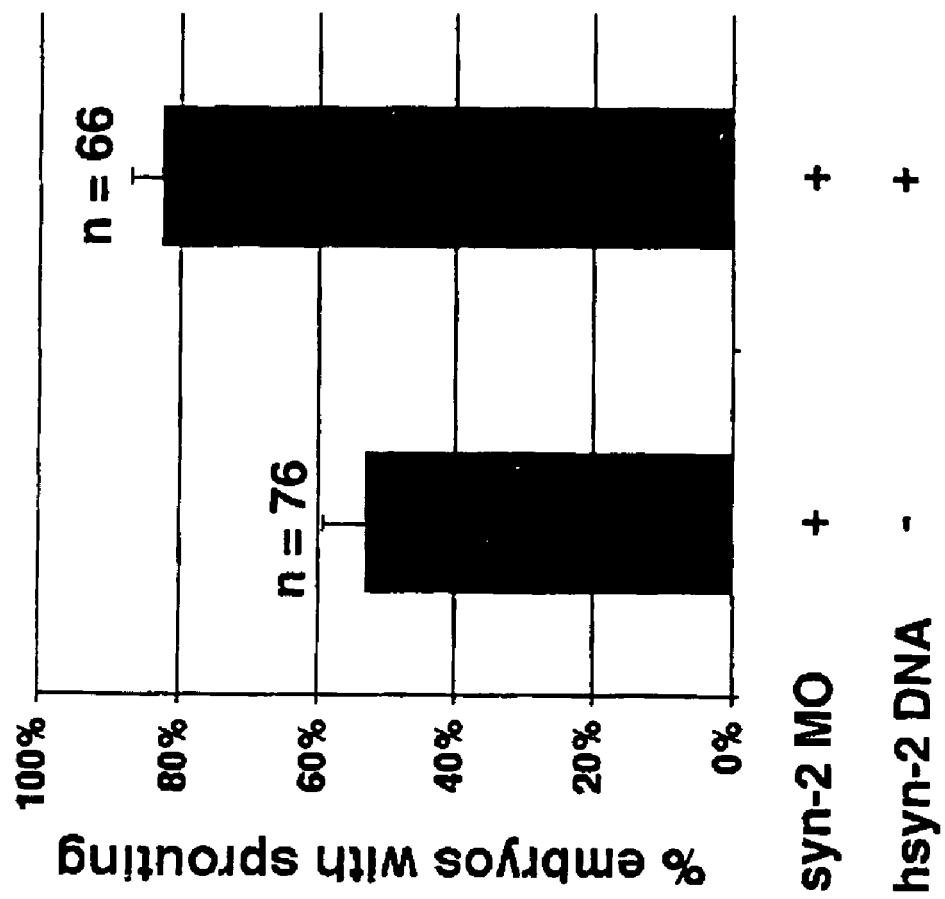

SYNDECANS AND ANGIOGENESIS

CROSS-REFERENCE TO RELATED APPLICATIONS

This application is a continuation of U.S. Ser. No. 10/866,589, filed Jun. 10, 2004 now abandoned.

STATEMENT AS TO FEDERALLY SPONSORED RESEARCH

Funding for the work described herein was provided in part by the National Institutes of Health, grant numbers GM55877 and GM63904. The federal government may have certain rights in the invention.

TECHNICAL FIELD

The invention relates to methods and materials for modulating angiogenesis in an animal by modulating the expression or activity of syndecan-2.

BACKGROUND

Proteoglycans are widely distributed, membrane-anchored glycoproteins that have covalently linked extracellular sidechains containing glycosaminoglycan (GAG) molecules such as heparan sulfate, a polymer of repeating disaccharide subunits. GAG side chains can be of different lengths and are subject to modification by sulfation and epimerization, and their structures serve as specific recognition sites for various ligands, including growth factors, extracellular matrix components, and other cell surface molecules. Heparan sulfate proteoglycans have been implicated in the regulation of numerous cellular processes, including coagulation cascades, growth factor signaling, lipase binding and activity, cell adhesion to the extracellular matrix and subsequent cytoskeletal organization, proliferation, differentiation, inflammation, microbial invasion, and tumor metastasis.

The syndecans make up a class of the heparan sulfate proteoglycans that are present on most cell types. Syndecans appear to play modulatory roles as coreceptors by presenting growth factors to their primary receptors or by increasing the infectivity of viruses by interacting with their primary receptors. See, Woods (2001) *J. Clin. Invest.* 107:935-941; and Elenius and Jalkanen (1994) *J. Cell Sci.* 107:2975-2982. Syndecans also have been implicated in neurite outgrowth, limb development, cell adhesion, and epithelial morphogenesis.

SUMMARY

The invention is based on the cloning of the zebrafish syndecan-2 gene (ec2) and the discovery that the encoded protein, EC2, is involved in vasculogenesis and angiogenesis. This discovery indicates that modulation of syndecan levels would be useful for treating clinical conditions associated with excessive or impaired angiogenesis and vasculogenesis. The invention therefore features materials and methods for modulating angiogenesis and vasculogenesis by modulating the expression or function of syndecan polypeptides.

In one aspect, the invention features a method for inhibiting angiogenesis in a vertebrate. The method can include administering to the vertebrate an effective amount of a cytoplasmically truncated Syndecan-2 polypeptide. The truncated Syndecan-2 polypeptide can be a dominant negative Syndecan-2 polypeptide (e.g., a polypeptide containing amino acids 1 to 193 of the sequence set forth in SEQ D NO:2).

In another aspect, the invention features a method for inhibiting angiogenesis in a vertebrate. The method can include administering to the vertebrate an effective amount of a nucleic acid containing a sequence that encodes a cytoplasmically truncated Syndecan-2 polypeptide. The construct can be expressed in the vertebrate to produce the truncated Syndecan-2 polypeptide. The truncated Syndecan-2 polypeptide can be a dominant negative Syndecan-2 polypeptide (e.g., a polypeptide containing amino acids 1 to 193 of the sequence set forth in SEQ ID NO:2).

In another aspect, the invention features a method for killing a tumor cell. The method can include contacting the tumor cell with a cytoplasmically truncated Syndecan-2 polypeptide. The contacting can include administering to the tumor cell a nucleic acid containing a sequence that encodes the cytoplasmically truncated Syndecan-2 polypeptide. The construct can be expressed in the tumor cell to produce the truncated Syndecan-2 polypeptide. The truncated Syndecan-2 polypeptide can be a dominant negative Syndecan-2 polypeptide (e.g., a polypeptide containing amino acids 1 to 193 of the sequence set forth in SEQ ID NO:2). The tumor cell can be present in a breast tumor, a lung tumor, or a prostate tumor. The method can further include monitoring the size of the tumor.

The invention also features a method for inhibiting tumor growth. The method can include contacting the tumor with a cytoplasmically truncated Syndecan-2 polypeptide. The contacting can include administering to the tumor a nucleic acid comprising a sequence that encodes the cytoplasmically truncated Syndecan-2 polypeptide. The construct can be expressed in a cell of the tumor to produce the truncated Syndecan-2 polypeptide. The truncated Syndecan-2 polypeptide can be a dominant negative Syndecan-2 polypeptide (e.g., a polypeptide containing amino acids 1 to 193 of the sequence set forth in SEQ ID NO:2). The tumor cell can be present in a breast tumor, a lung tumor, or a prostate tumor. The method can further include monitoring the size of the tumor.

In addition, the invention features an antisense polynucleotide effective to decrease expression from a nucleic acid molecule encoding a syndecan-2 polypeptide. The antisense polynucleotide can be a polynucleotide analogue (e.g., a morpholino-modified polynucleotide). The antisense polynucleotide can contain nucleotide the sequence of SEQ ID NO:9, SEQ ID NO:10, or SEQ ID NO:11. The syndecan-2 polypeptide can be a human syndecan-2 polypeptide.

In another aspect, the invention features a cell containing an antisense polynucleotide effective to decrease expression from a nucleic acid molecule encoding a syndecan-2 polypeptide.

The invention also features a teleost embryo containing a morpholino-modified antisense polynucleotide effective to decrease expression from a nucleic acid molecule encoding a syndecan-2 polypeptide, wherein the decreased expression results in an alteration of angiogenesis in the embryo. The teleost embryo can be selected from the group consisting of a zebrafish embryo, a stickleback embryo, a medaka embryo, and a puffer fish embryo.

In another aspect, the invention features an isolated nucleic acid having the nucleotide sequence of SEQ ID NO:1. The invention also features an expression vector containing a polynucleotide sequence operably linked to an expression control sequence, wherein the expression control sequence directs production of a transcript from the polynucleotide sequence, and wherein the transcript is capable of hybridizing under conditions of high stringency to a target nucleic acid molecule having the nucleotide sequence of SEQ ID NO:1 or having the complement of SEQ ID NO:1.

In yet another aspect, the invention features a purified polypeptide containing the amino acid sequence of SEQ ID NO:2.

In still another aspect, the invention features a purified antibody that binds specifically to a polypeptide containing the amino acid sequence of SEQ ID NO:2. The invention also features a method for making an antibody. The method can include immunizing a non-human animal with an immunogenic fragment of a polypeptide having the amino acid sequence of SEQ ID NO:2. Alternatively, the method can include providing a hybridoma cell that produces a monoclonal antibody specific for a polypeptide with the amino acid sequence of SEQ ID NO:2, and culturing the cell under conditions that permit production of the monoclonal antibody.

In another aspect, the invention features a method for identifying a syndecan-2-modulating agent. The method can include: a) contacting a candidate agent with a living cell preparation producing a syndecan-2 polypeptide; b) detecting the amount of syndecan-2 polypeptide in the living cell preparation subsequent to step (a); and c) identifying the candidate agent as a syndecan-2-modulating agent if the amount of syndecan-2 polypeptide in the living cell preparation is specifically increased or decreased relative to a control living cell preparation.

In still another aspect, the invention features a method for identifying an angiogenesis-modulating agent. The method can include: a) contacting an animal with a syndecan-2-modulating agent; b) monitoring the animal for any alteration in angiogenesis; and c) identifying the syndecan-2-modulating agent as an angiogenesis-modulating agent if any alteration in angiogenesis is detected in step (b).

In another aspect, the invention features a method for making an angiogenesis-modulating agent. The method can include: a) contacting an animal with a syndecan-2-modulating agent; b) monitoring the animal for any alteration in angiogenesis; c) identifying the syndecan-2-modulating agent as an angiogenesis-modulating agent if any alteration in angiogenesis is detected in step (b); and d) producing the angiogenesis-modulating agent.

In a further aspect, the invention features a method for promoting angiogenesis in a vertebrate. The method can include administering to a vertebrate a functional syndecan-2 polypeptide or a nucleic acid encoding a functional syndecan-2 polypeptide. The vertebrate can be a mammal (e.g., a human). The administration can be topical administration (e.g., administration to the skin).

In another aspect, the invention features a method for reducing angiogenesis in a vertebrate. The method can involve administering to a vertebrate an antisense polynucleotide effective to decrease expression from a nucleic acid molecule encoding a syndecan-2 polypeptide.

In yet another aspect, the invention features a composition containing an antisense polynucleotide effective to decrease expression from a nucleic acid molecule encoding a syndecan-2 polypeptide.

In still another aspect, the invention features a method for detecting syndecan-2 expression in a tissue. The method can include contacting the tissue with a syndecan-2 probe and detecting binding of the probe to the tissue. The tissue can be a tumor tissue.

The invention also features an antisense polynucleotide effective to decrease expression from a nucleic acid molecule encoding a syndecan polypeptide. The antisense polynucleotide can be a polynucleotide analogue (e.g., a morpholino-modified polynucleotide.) The syndecan polypeptide can be syndecan-2, and the antisense polynucleotide can include the nucleotide sequence of SEQ ID NO:9, SEQ ID NO:10, or SEQ ID NO:11.

In another aspect, the invention provides a method for identifying a syndecan-modulating agent. The method can involve (a) contacting a candidate agent with a living cell preparation producing a syndecan polypeptide, (b) detecting the amount of the syndecan polypeptide in the living cell preparation subsequent to step (a), and (c) identifying the candidate agent as a syndecan-modulating agent if the amount of the syndecan polypeptide in the living cell preparation is specifically increased or decreased relative to a control living cell preparation. The syndecan polypeptide can be syndecan-2.

The invention also features a method for identifying an angiogenesis-modulating agent. A method can involve (a) contacting an animal with a syndecan-modulating agent, (b) monitoring the animal for any alteration in angiogenesis, and (c) identifying the syndecan-modulating agent as an angiogenesis-modulating agent if any alteration in angiogenesis is detected in step (b). The syndecan-modulating agent can be a syndecan-2-modulating agent.

In another aspect, the invention features a method for making an angiogenesis-modulating agent. The method can involve (a) contacting an animal with a syndecan-modulating agent, (b) monitoring the animal for any alteration in angiogenesis, (c) identifying the syndecan-modulating agent as an angiogenesis-modulating agent if any alteration in angiogenesis is detected in step (b), and (d) producing the angiogenesis-modulating agent. The syndecan-modulating agent can be a syndecan-2-modulating agent.

In yet another aspect, the invention features a method for promoting angiogenesis in a vertebrate. The method can involve administering to a vertebrate a functional syndecan polypeptide or a nucleic acid encoding a functional syndecan polypeptide. The syndecan polypeptide can be syndecan-2. The vertebrate can be a mammal (e.g., a human). The administration can be topical administration (e.g., administration to the skin).

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 1 is the nucleotide sequence of the zebrafish ec2 coding region and 5' untranslated region (SEQ ID NO:1). The start codon is in bold.

FIG. 2 is the amino acid sequence of the zebrafish EC2 polypeptide (SEQ ID NO:2).

FIG. 3 is an alignment of the mouse (m), rat (r), human (h), Xenopus (X), and zebrafish (z) syndecan-2 polypeptides (SEQ ID NO:3, SEQ ID NO:4, SEQ ID NO:5, SEQ ID NO:6, and SEQ ID NO:2, respectively).

FIGS. 4A and 4B are graphs showing the percentage of surviving embryos that exhibit dorsal curvature following injection with various ec2 morpholinos.

FIGS. 10A and 10B are graphs showing the percentage of surviving embryos with reduced flk-1 expression after injection with vectors encoding a cytoplasmically-truncated form of EC2 or full-length EC2, either alone or in combination with a GFP expression vector or an ec2 morpholino.

FIG. 11 is a graph showing the percentage of surviving embryos exhibiting new sprouts of intersegmental vessels after injection with an ec2 morpholino alone or in combination with a human syndecan-2 expression construct.

DETAILED DESCRIPTION

Figure 4B:
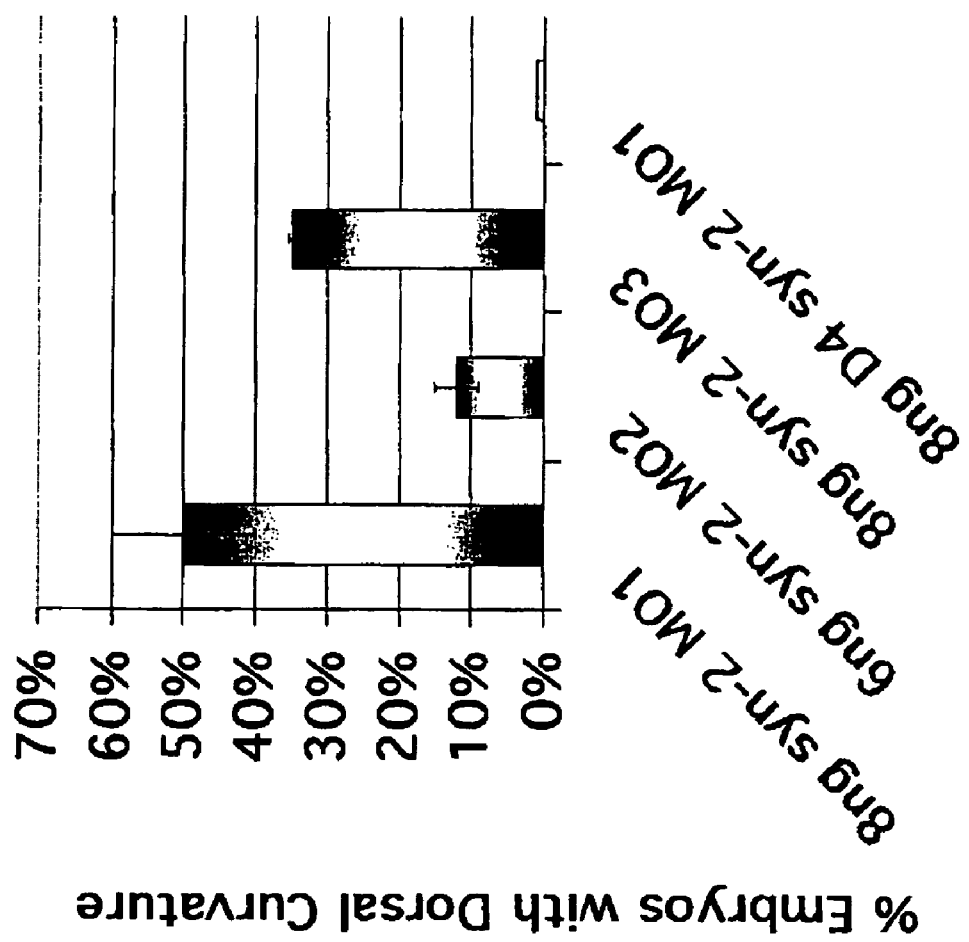

The discovery that the zebrafish homologue of syndecan-2 (EC2; also referred to herein as Syndecan-2) is involved in angiogenesis indicates that angiogenesis can be modulated by increasing or decreasing cellular levels of functional syndecan polypeptides (e.g., EC2). In addition to ec2 nucleic acids and syndecan polypeptides, the subsections below provide methods for identifying agents that increase or decrease the biological effects of syndecans by increasing or decreasing syndecan expression or by enhancing or inhibiting syndecan function. Similarly, methods for identifying angiogenesis-modulating agents are disclosed; agents that decrease syndecan expression or syndecan function can reduce angiogenesis, for example, and syndecan-2 nucleic acids or syndecan polypeptides can be used to stimulate angiogenesis. By modulating the expression or function of syndecans, disease conditions that are associated with angiogenesis can be managed.

1. Nucleic Acids

As used herein, the term "nucleic acid" refers to both RNA and DNA, including cDNA, genomic DNA, and synthetic (e.g., chemically synthesized) DNA. A nucleic acid molecule can be double-stranded or single-stranded (i.e., a sense or an antisense single strand). Nucleic acids of the invention include, for example, a zebrafish ec2 DNA, which can contain the nucleotide sequence of SEQ ID NO:1 and thus encode an EC2 polypeptide having the amino acid sequence of SEQ ID NO:2.

An "isolated nucleic acid" refers to a nucleic acid that is separated from other nucleic acid molecules that are present in a vertebrate genome, including nucleic acids that normally flank one or both sides of the nucleic acid in a vertebrate genome (e.g., nucleic acids that flank the ec2 gene). The term "isolated" as used herein with respect to nucleic acids also includes any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided at least one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not considered an isolated nucleic acid.

Isolated nucleic acid molecules of the invention can be produced by standard techniques, including, without limitation, common molecular cloning and chemical nucleic acid synthesis techniques. For example, polymerase chain reaction (PCR) techniques can be used to obtain an isolated ec2 nucleic acid molecule. Isolated nucleic acids of the invention also can be chemically synthesized, either as a single nucleic acid molecule (e.g., using automated DNA synthesis in the 3' to 5' direction using phosphoramidite technology) or as a series of polynucleotides. For example, one or more pairs of long polynucleotides (e.g., >100 nucleotides) can be synthesized that contain the desired sequence, with each pair containing a short segment of complementarity (e.g., about 15 nucleotides) such that a duplex is formed when the polynucleotide pair is annealed. DNA polymerase is used to extend the polynucleotides, resulting in a single, double-stranded nucleic acid molecule per polynucleotide pair.

Nucleic acids of the invention can be incorporated into vectors. As used herein, a "vector" is a replicon, such as a plasmid, phage, or cosmid, into which another nucleic acid segment may be inserted so as to bring about replication of the inserted segment. Vectors of the invention typically are expression vectors containing an inserted nucleic acid segment that is operably linked to expression control sequences.

An "expression vector" is a vector that includes one or more expression control sequences, and an "expression control sequence" is a DNA sequence that controls and regulates the transcription and/or translation of another DNA sequence. Expression control sequences include, for example, promoter sequences, transcriptional enhancer elements, and any other nucleic acid elements required for RNA polymerase binding, initiation, or termination of transcription. With respect to expression control sequences, "operably linked" means that the expression control sequence and the inserted nucleic acid sequence of interest are positioned such that the inserted sequence is transcribed (e.g., when the vector is introduced into a host cell).

2. Polynucleotides and Polynucleotide Analogues

"Polynucleotides" are nucleic acid molecules of at least three nucleotide subunits. A nucleotide has three components: an organic base (e.g., adenine, cytosine, guanine, or thymine, herein referred to as A, C, G, and T, respectively), a phosphate group, and a five-carbon sugar that links the phosphate group and the organic base. In a polynucleotide, the organic bases of the nucleotide subunits determine the sequence of the polynucleotide and allow for interaction with a second polynucleotide. The nucleotide subunits of a polynucleotide are linked by phophodiester bonds such that the five-carbon sugar of one nucleotide forms an ester bond with the phosphate of an adjacent nucleotide, and the resulting sugar-phosphates form the backbone of the polynucleotide.

"Polynucleotide analogues" are chemically modified polynucleotides. In some embodiments, polynucleotide analogues can be generated by replacing portions of the sugar-phosphate backbone of a polynucleotide with alternative functional groups. Morpholino-modified polynucleotides, referred to herein as "morpholinos," are polynucleotide analogues in which the bases are linked by a morpholino-phosphorodiamidate backbone (See, Summerton and Weller (1997) *Antisense Nuc. Acid Drug Devel.* 7:187-195; and U.S. Pat. Nos. 5,142,047 and 5,185,444).

In addition to morpholinos, other examples of polynucleotide analogues include analogues in which the bases are linked by a polyvinyl backbone (Pitha et al. (1970) *Biochim. Biophys. Acta* 204:39-48; Pitha et al. (1970) *Biopolymers* 9:965-977), peptide nucleic acids (PNAs) in which the bases are linked by amide bonds formed by pseudopeptide 2-aminoethyl-glycine groups (Nielsen et al. (1991) *Science* 254: 1497-1500), analogues in which the nucleoside subunits are linked by methylphosphonate groups (Miller et al. (1979) *Biochem.* 18:5134-5143; Miller et al. (1980) *J. Biol. Chem.* 255:9659-9665), analogues in which the phosphate residues linking nucleoside subunits are replaced by phosphoroamidate groups (Froehler et al. (1988) *Nucleic Acids Res.* 156: 4831-4839), and phosphorothioated DNAs, analogues containing sugar moieties that have 2' O-methyl groups (Cook (1998) *Antisense Medicinal Chemistry*, Springer, New York, pp. 51-101).

Polynucleotides of the invention can be produced through the well-known and routinely used technique of solid phase synthesis. Equipment for such synthesis is commercially available from several vendors including, for example, Applied Biosystems (Foster City, Calif.). Alternatively, other suitable methods for such synthesis can be used (e.g., common molecular cloning and chemical nucleic acid synthesis techniques). Similar techniques also can be used to prepare polynucleotide analogues such as morpholinos or phosphorothioate derivatives. In addition, polynucleotides and polynucleotide analogues can be obtained commercially from, for example, Gene Tools, L.L.C. (Philomath, Oreg.) or Oligos Etc. (Wilsonville, Oreg.).

Typically, polynucleotide analogues such as morpholinos are single stranded. Polynucleotide analogues can be of various lengths (e.g., from 8 bases in length to more than 112 bases in length, typically from 12 to 72 bases in length). Morpholinos can be, for example, 15 to 45 bases in length (e.g., 18 to 30 bases in length). Polynucleotide analogues can be designed to contain certain percentages of each base type (e.g., 40-60% A/T content and 40-60% G/C content, or 50% A/T content and 50% G/C content). In addition, it is particularly useful to avoid sequences containing four or more consecutive G residues, as well as secondary structures such as hairpins.

Polynucleotides and polynucleotide analogues of the present invention (e.g., morpholinos) can be designed to hybridize to a target nucleic acid molecule of known sequence (e.g., a nucleic acid molecule encoding EC2 or another syndecan-2 polypeptide). As described herein, a polynucleotide analogue can have the nucleotide sequence set forth in SEQ ID NO:9, 10, or 11, for example. The term "hybridization," as used herein, means hydrogen bonding, which can be Watson-Crick, Hoogsteen, or reversed Hoogsteen hydrogen bonding, between complementary nucleoside or nucleotide bases. For example, A and T, and G and C, respectively, are complementary bases that pair through the formation of hydrogen bonds. "Complementary," as used herein, refers to the capacity for precise pairing between two nucleotides. For example, if a nucleotide at a certain position of a polynucleotide analogue is capable of hydrogen bonding with a nucleotide at the same position of a target nucleic acid molecule, then the polynucleotide analogue and the target nucleic acid molecule are considered to be complementary to each other at that position. A polynucleotide or polynucleotide analogue and a target nucleic acid molecule are complementary to each other when a sufficient number of corresponding positions in each molecule are occupied by nucleotides that can hydrogen bond with each other. The term "specifically hybridizable" is used to indicate a sufficient degree of complementarity or precise pairing such that stable and specific binding occurs between the polynucleotide or polynucleotide analogue and the target nucleic acid molecule.

It is understood in the art that the sequence of the polynucleotide or polynucleotide analogue need not be 100% complementary to that of the target nucleic acid molecule to be specifically hybridizable. A polynucleotide or polynucleotide analogue is specifically hybridizable when (a) binding of the polynucleotide or polynucleotide analogue to the target nucleic acid molecule interferes with the normal function of the target nucleic acid molecule, and (b) there is sufficient complementarity to avoid non-specific binding of the polynucleotide or polynucleotide analogue to non-target sequences under conditions in which specific binding is desired, i.e., under conditions in which in vitro assays are performed or under physiological conditions for in vivo assays or therapeutic uses.

Hybridization conditions in vitro are dependent on temperature, time, and salt concentration [see, e.g., Sambrook et al., *Molecular Cloning: A Laboratory Manual*, Cold Spring Harbor Laboratory Press, NY (1989)]. Typically, conditions of high to moderate stringency are used for specific hybridization in vitro, such that hybridization occurs between substantially similar nucleic acids, but not between dissimilar nucleic acids. Specific high stringency hybridization conditions are hybridization in 5×SSC (0.75 M sodium chloride/ 0.075 M sodium citrate) for 1 hour at 40° C. with shaking, followed by washing 10 times in 1×SSC at 40° C. and 5 times in 1×SSC at room temperature.

In vivo hybridization conditions consist of intracellular conditions (e.g., physiological pH and intracellular ionic conditions) that govern the hybridization of polynucleotides and polynucleotide analogues with target nucleic acid molecules. In vivo conditions can be mimicked in vitro by relatively low stringency conditions. For example, hybridization can be carried out in vitro in 2×SSC (0.3 M sodium chloride/0.03 M sodium citrate), 0.1% SDS at 37° C. Alternatively, a wash solution containing 4×SSC, 0.1% SDS can be used at 37° C., with a final wash in 1×SSC at 45° C. In order for a polynucleotide or polynucleotide analogue to specifically decrease expression from a target nucleic acid molecule, the polynucleotide or polynucleotide analogue must hybridize specifically to the target nucleic acid molecule under physiological conditions.

A polynucleotide or polynucleotide analogue can be complementary to a sense or an antisense target nucleic acid molecule. When complementary to a sense nucleic acid molecule, the polynucleotide analogue is said to be antisense. When complementary to an antisense nucleic acid molecule, the polynucleotide analogue is said to be sense. For example, a polynucleotide analogue can be antisense to an mRNA molecule or sense to the DNA molecule from which an mRNA is transcribed. As used herein, the term "coding region" refers to the portion of a nucleic acid molecule encoding an RNA molecule that is translated into protein. A polynucleotide or polynucleotide analogue can be complementary to the coding region of an mRNA molecule or the region corresponding to the coding region on the antisense DNA strand. Alternatively, a polynucleotide or polynucleotide analogue can be complementary to the non-coding region of a nucleic acid molecule. Examples of such polynucleotide analogues (morpholinos ec2-MO#2 and ec2-MO#3) are described in Example 4, below. A non-coding region can be, for example, upstream of a transcriptional start site or downstream of a transcriptional end-point in a DNA molecule. A non-coding region also can be upstream of the translational start codon or downstream of the stop codon in an mRNA molecule. Furthermore, a polynucleotide or polynucleotide analogue can be complementary to both coding and non-coding regions of a target nucleic acid molecule. For example, a polynucleotide analogue can be complementary to a region that includes a portion of the 5' untranslated region (5'-UTR) leading up to the start codon, the start codon, and coding sequences immediately following the start codon of a target nucleic acid molecule. Such a polynucleotide analogue (morpholino ec2-MO#1) also is described in Example 4, below.

Polynucleotides and polynucleotide analogues of the invention can be useful for research and diagnostics, and for therapeutic use. For example, assays based on hybridization of polynucleotide analogues to nucleic acids encoding EC2 can be used to evaluate levels of EC2 in a tissue sample. Hybridization of a polynucleotide analogue of the invention with a target nucleic acid molecule can be detected by a number of methods. Some of these methods are well known in the art, and including detection by conjugating an enzyme to the polynucleotide analogues or by radiolabeling of the polynucleotide analogues. Any other suitable means of detection also can be used. Additionally, polynucleotides and polynucleotide analogues can be employed as therapeutic moieties in the treatment of disease states in animals, including humans (see subsection 6, below).

3. Polypeptides

The invention provides purified syndecan polypeptides. A "polypeptide" refers to a chain of amino acid residues, regardless of post-translational modification (e.g., phosphorylation or glycosylation). Proteoglycans therefore also are referred to herein as polypeptides. Polypeptides of the invention are at least 60 amino acids in length (e.g., 60, 65, 70, 100, or more than 100 amino acids in length), and are capable of eliciting a syndecan-specific antibody response (i.e., are able to act as immunogens that induce the production of antibodies capable of specific binding to a syndecan).

The syndecans make up a class of heparan sulfate proteoglycans. A newly identified polypeptide can be classified as belonging to the syndecan family of polypeptides based on amino acid sequence comparison with known syndecan polypeptides. For example, a newly identified polypeptide belongs to the syndecan class of proteoglycans if it is more similar in amino acid sequence to any member of the syndecan family of polypeptides than the two least similar members within the syndecan family. As used herein, the term "syndecan polypeptide" refers to a polypeptide belonging to the syndecan class of proteoglycans. The zebrafish EC2 polypeptide therefore is a syndecan polypeptide. Furthermore, a syndecan polypeptide according to the present invention can have the amino acid sequence provided in SEQ ID NO:2, or the amino acid sequence of a portion of SEQ ID NO:2 provided that it is at least 60 amino acids in length (e.g., at least 60, at least 70, or at least 80 amino acids in length) and is a syndecan-specific immunogen. As used herein, a "functional syndecan polypeptide" is a syndecan polypeptide that is capable of promoting angiogenesis (see subsection 6, below).

A syndecan polypeptide can be a dominant negative syndecan polypeptide. For example, a syndecan polypeptide can be a cytoplasmically truncated form of Syndecan-2. In one embodiment, a cytoplasmically truncated form of Syndecan-2 is encoded by nucleotides 65 to 644 of the sequence set forth in SEQ ID NO:1. This embodiment, designated herein as δS2, contains amino acids 1-193 of the sequence set forth in SEQ ID NO:2, and is a dominant negative form of Syndecan-2. In other embodiments, a cytoplasmically truncated form of Syndecan-2 can contain between 180 and 205 (e.g., between 185 and 200, or between 190 and 195) amino acids. Such syndecan polypeptides can be useful to inhibit angiogenesis, as described herein.

Syndecan polypeptides can be produced by a number of methods, many of which are well known in the art. By way of example and not limitation, syndecan polypeptides can be obtained by extraction from a natural source (e.g., from isolated cells, tissues or bodily fluids), by expression of a recombinant nucleic acid encoding the polypeptide, or by chemical synthesis.

Syndecan polypeptides of the invention can be produced by, for example, standard recombinant technology, using expression vectors encoding syndecan polypeptides (e.g., an expression vector containing EC2 coding sequences). Expression vectors can be introduced into host cells (e.g., by transformation or transfection) for expression of the encoded polypeptide, which then can be purified. Expression systems that can be used for small or large scale production of syndecan polypeptides include, without limitation, microorganisms such as bacteria (e.g., E. coli and B. subtilis) transformed with recombinant bacteriophage DNA, plasmid DNA, or cosmid DNA expression vectors containing the nucleic acid molecules of the invention; yeast (e.g., S. cerevisiae) transformed with recombinant yeast expression vectors containing the nucleic acid molecules of the invention; insect cell systems infected with recombinant virus expression vectors (e.g., baculovirus) containing the nucleic acid molecules of the invention; plant cell systems infected with recombinant virus expression vectors (e.g., tobacco mosaic virus) or transformed with recombinant plasmid expression vectors (e.g., Ti plasmid) containing the nucleic acid molecules of the invention; or mammalian cell systems (e.g., primary cells or immortalized cell lines such as COS cells, Chinese hamster ovary cells, HeLa cells, human embryonic kidney 293 cells, and 3T3 L1 cells) harboring recombinant expression constructs containing promoters derived from the genome of mammalian cells (e.g., the metallothionein promoter) or from mammalian viruses (e.g., the adenovirus late promoter and the cytomegalovirus promoter), along with the nucleic acids of the invention.

The term "purified" as used herein with reference to a polypeptide refers to a polypeptide that either has no naturally occurring counterpart (e.g., a peptidomimetic), or has been chemically synthesized and is thus uncontaminated by other polypeptides, or has been separated or purified from other cellular components by which it is naturally accompanied (e.g., other cellular proteins, polynucleotides, or cellular components). Typically, the polypeptide is considered "purified" when it is at least 70%, by dry weight, free from the proteins and naturally occurring organic molecules with which it naturally associates. A preparation of the purified polypeptide of the invention therefore can be, for example, at least 80%, at least 90%, or at least 99%, by dry weight, the polypeptide of the invention.

Suitable methods for purifying the syndecan polypeptides of the invention include, for example, affinity chromatography, immunoprecipitation, size exclusion chromatography, and ion exchange chromatography. See, for example, Flohe et al. (1970) *Biochim. Biophys. Acta.* 220:469-476, or Tilgmann et al. (1990) *FEBS* 264:95-99. The extent of purification can be measured by any appropriate method, including but not limited to: column chromatography, polyacrylamide gel electrophoresis, or high-performance liquid chromatography. Syndecan polypeptides also can be "engineered" to contain a tag sequence (e.g., a polyhistidine tag, a myc tag, or a Flag®0 tag) that allows the polypeptide to be purified (e.g., captured onto an affinity matrix). Immunoaffinity chromatography also can be used to purify syndecan polypeptides.

4. Antibodies

The invention also provides antibodies having specific binding activity for syndecan polypeptides (e.g., EC2 or another syndecan-2 polypeptide). Such antibodies can be useful for detecting levels of the EC2 polypeptide in cells treated with morpholinos, for example. Syndecan antibodies also can be useful as syndecan-modulating agents (see subsection 5, below). As described above, a syndecan polypeptide of the invention can act as an immunogen to elicit an antibody response that is specific to EC2, for example, and does not cross-react with a different polypeptide. A specific antibody directed to a syndecan polypeptide therefore will specifically recognize that syndecan, without substantial binding or hybridizing to other polypeptides that may be present in the same biological sample.

An "antibody" or "antibodies" includes intact molecules as well as fragments thereof that are capable of binding to an epitope of a syndecan polypeptide. The term "epitope" refers to an antigenic determinant on an antigen to which an antibody binds. Epitopes usually consist of chemically active surface groupings of molecules such as amino acids or sugar side chains, and typically have specific three-dimensional structural characteristics, as well as specific charge characteristics. Epitopes generally have at least five contiguous amino acids. The terms "antibody" and "antibodies" include polyclonal antibodies, monoclonal antibodies, humanized or chimeric antibodies, single chain Fv antibody fragments, Fab fragments, and F(ab)$_2$ fragments. Polyclonal antibodies are heterogeneous populations of antibody molecules that are specific for a particular antigen, while monoclonal antibodies are homogeneous populations of antibodies to a particular epitope contained within an antigen. Monoclonal antibodies are particularly useful.

In general, a syndecan polypeptide is produced as described above, i.e., recombinantly, by chemical synthesis, or by purification of the native protein, and then used to immunize animals. Various host animals including, for example, rabbits, chickens, mice, guinea pigs, and rats, can be immunized by injection of the protein of interest. Depending on the host species, adjuvants can be used to increase the immunological response. These include Freund's adjuvant (complete and/or incomplete), mineral gels such as aluminum hydroxide, surface-active substances such as lysolecithin, pluronic polyols, polyanions, peptides, oil emulsions, keyhole limpet hemocyanin, and dinitrophenol. Polyclonal antibodies are contained in the sera of the immunized animals. Monoclonal antibodies can be prepared using standard hybridoma technology. In particular, monoclonal antibodies can be obtained by any technique that provides for the production of antibody molecules by, for example, continuous cell lines in culture as described by Kohler et al. [(1975) *Nature* 256:495-497]; the human B-cell hybridoma technique of Kosbor et al. [(1983) *Immunology Today* 4:72] and Cote et al. [(1983) *Proc. Natl. Acad. Sci. USA* 80:2026-2030]; and the EBV-hybridoma technique of Cole et al. [*Monoclonal Antibodies and Cancer Therapy*, Alan R. Liss, Inc. pp. 77-96 (1983)]. Such antibodies can be of any immunoglobulin class, including IgM, IgG, IgE, IgA, IgD, and any subclass thereof. A hybridoma producing the monoclonal antibodies of the invention can be cultivated in vitro or in vivo.

A chimeric antibody is a molecule in which different portions are derived from different animal species, such as those having a variable region derived from a mouse monoclonal antibody and a human immunoglobulin constant region. Chimeric antibodies can be produced through standard techniques.

Antibody fragments that have specific binding affinity for syndecan polypeptides can be generated by known techniques. Such antibody fragments include, but are not limited to, F(ab')$_2$ fragments that can be produced by pepsin digestion of an antibody molecule, and Fab fragments that can be generated by deducing the disulfide bridges of F(ab')$_2$ fragments. Alternatively, Fab expression libraries can be constructed. See, for example, Huse et al. (1989) *Science* 246:1275-1281. Single chain Fv antibody fragments are formed by linking the heavy and light chain fragments of the Fv region via an amino acid bridge (e.g., 15 to 18 amino acids), resulting in a single chain polypeptide. Single chain Fv antibody fragments can be produced through standard techniques, such as those disclosed in U.S. Pat. No. 4,946,778.

A monoclonal antibody also can be obtained by using commercially available kits that aid in preparing and screening antibody phage display libraries. An antibody phage display library is a library of recombinant combinatorial immunoglobulin molecules. Examples of kits that can be used to prepare and screen antibody phage display libraries include the Recombinant Phage Antibody System (Pharmacia, Peapack, N.J.) and SurfZAP Phage Display Kit (Stratagene, La Jolla, Calif.).

Once produced, antibodies or fragments thereof can be tested for recognition of a syndecan polypeptide by standard immunoassay methods including, for example, enzyme-linked immunosorbent assay (ELISA) or radioimmuno assay (RIA). See, *Short Protocols in Molecular Biology*, eds. Ausubel et al., Green Publishing Associates and John Wiley & Sons (1992). Antibodies that have equal binding affinities for recombinant and native proteins are particularly useful.

5. Syndecan-modulating Agents

The invention provides methods for identifying substances that specifically increase or decrease the amount of a syndecan polypeptide in a cell, tissue, organ, or organism of interest. A substance that specifically increases or decreases the amount of a syndecan polypeptide is herein referred to as a "syndecan-modulating agent." The amount of a syndecan polypeptide in a cell can be assessed by, for example, conventional antibody-based assays. Alternatively, the amount of a syndecan polypeptide can be estimated by detecting syndecan RNA using conventional nucleic acid-based assays [e.g., northern blotting or reverse transcription-polymerase chain reaction (RT-PCR)]. The amount of a syndecan polypeptide in a cell can be modulated by increasing or decreasing the production of syndecan mRNA or the amount of functional syndecan polypeptide.

Polynucleotide analogues of the invention can be used to alter expression from a target syndecan nucleic acid and thus can be syndecan-modulating agents. For example, a morpholino targeted to ec2 can be used to decrease production of EC2, while a morpholino targeted to a human syndecan-2 nucleic acid can be used to decrease production of human syndecan-2 protein. As used herein, the term "expression" with respect to a nucleic acid molecule refers to production of an mRNA molecule from a DNA molecule as well as production of a polypeptide from an mRNA molecule. Expression from a nucleic acid molecule can be decreased, for example, by interfering with (1) any process necessary for mRNA transcription (e.g., binding of RNA polymerase, binding of transcription factors, or transcriptional elongation of the mRNA); (2) mRNA processing (e.g., capping or splicing); (3) mRNA transport across the nuclear membrane; or (4) any process necessary for mRNA translation (e.g., ribosome binding or translational initiation, elongation, or termination). Expression also can be decreased by inducing the cellular nuclease system that degrades cognate mRNAs. In an RNaseH dependent mechanism, for example, a double stranded target mRNA/polynucleotide analogue is degraded by RNaseH. In addition to polynucleotide analogues, conventional polynucleotides can be used to alter expression from target nucleic acid molecules to which they are complementary.

As used herein, a "decrease" with respect to expression from a target nucleic acid molecule refers to a decrease that can be detected by assessing changes in mRNA or protein levels. For example, a decrease can refer to a 5%, 10%, 25%, 50%, 75%, or more than a 75% decrease in expression. A decrease in expression also includes complete inhibition of expression, whereby a 100% decrease in expression from a nucleic acid molecule is achieved. Changes in mRNA and protein levels can be detected and/or measured by any of a number of methods known in the art, including but not limited to northern blotting or RT-PCR for mRNA assessment, and western blotting or enzyme-linked immunosorbent assays (ELISA) for protein assessment. Other suitable methods also can be used to assess mRNA and protein levels.

A decrease in expression from a target syndecan nucleic acid molecule can be achieved using one polynucleotide analogue. A decrease in expression from a target syndecan nucleic acid molecule also can be achieved using two polynucleotide analogues having different sequences and therefore being complementary to different portions of the same target nucleic acid molecule. A single polynucleotide analogue can be used to simultaneously decrease expression from two or more syndecan nucleic acid molecules that are closely related. In addition, multiple polynucleotide analogues having sequences complementary to more than one target syndecan nucleic acid molecule can be used to decrease expression from multiple target nucleic acid molecules at the same time.

Polynucleotide analogues such as morpholinos can be delivered to a living cell, tissue, organ, or organism of interest by methods used to deliver single stranded mRNA, such as the methods described in Hyatt and Ekker (1999) *Meth. Cell Biol.* 59:117-126. Non-limiting examples of delivery methods include (1) microinjection (e.g., as described in Example 4, below), and (2) simply exposing the cell, tissue, organ, or organism of interest to the polynucleotide analogue. A cell can be, for example, a fertilized or unfertilized egg, or a cell in culture. A tissue can be any tissue regardless of its state of differentiation, and can include, for example, tumor tissue or normal tissue from an organism such as a mammal or a fish. An organ can be, for example, thymus, bone marrow, pancreas, heart, or the blood vessels of the vasculature. Non-limiting examples of organisms include vertebrate embryos such as teleost embryos, juvenile animals, or adult animals. Examples of teleost embryos include zebrafish embryos, puffer fish embryos, medaka embryos, and stickleback embryos.

Polynucleotide analogues can be delivered in a suitable buffer. A suitable buffer is one in which the polynucleotide analogue can be dissolved, and which is non-toxic to the cell, tissue, organ, or organism to which the polynucleotide analogue is to be delivered. A non-toxic buffer can be one that is isotonic to the organism or cell of interest. For example, morpholinos can be dissolved in Danieau buffer (see Example 4, below) for injection into zebrafish eggs or embryos.

Alternatively, a polynucleotide designed to hybridize to a target syndecan nucleic acid molecule can be inserted into an expression vector that is then introduced into the cell, tissue, or organism of interest. For example, a polynucleotide in an expression vector can be operably linked to an expression control sequence, which will direct the production of a polynucleotide transcript that is capable of hybridizing to a target nucleic acid molecule. Methods for introducing a vector into a cell or an organism are known in the art (e.g., transformation, transfection, and microinjection).

To identify syndecan-modulating agents, a cell that produces syndecan polypeptides can be contacted with a candidate agent (e.g., a morpholino designed to hybridize to a target nucleic acid molecule encoding EC2), and the amount of the syndecan polypeptide or mRNA encoding the syndecan polypeptide can be determined. A syndecan-modulating agent is one that causes an increase or decrease in the amount of syndecan polypeptide relative to a control cell preparation that was not contacted by the candidate agent. As described above, the term "increase" or "decrease" refers to any detectable change in the amount of syndecan polypeptide (e.g., a 3%, 6%, 12%, or greater than 12% increase or decrease in the amount of syndecan polypeptide). A syndecan-modulating agent that is specific will cause an increase or decrease in the functional amount of only the polypeptide encoded by the target nucleic acid; polypeptides encoded by other nucleic acid sequences will not be affected.

Examples of syndecan-modulating agents that decrease levels of syndecan polypeptides include morpholinos (e.g.

those described in the Examples, below) and antibodies against syndecans. Examples of syndecan-modulating agents that increase levels of syndecan polypeptides include syndecan polypeptides and nucleic acids encoding syndecan polypeptides.

6. Angiogenesis-modulating Agents

Angiogenesis refers to the generation of new blood vessels. Under normal physiological conditions, angiogenesis occurs during wound healing, during tissue and organ regeneration, during embryonic vasculature development, and during formation of the corpus luteum, endometrium, and placenta. Excessive angiogenesis, however, has been associated with a number of disease conditions. Examples of diseases associated with excessive angiogenesis include rheumatoid arthritis, atherosclerosis, diabetes mellitus, retinopathies, psoriasis, and retrolental fibroplasia. In addition, angiogenesis has been identified as a critical requirement for solid tumor growth and cancer metastasis. Examples of tumor types associated with angiogensis include rhabdomyosarcomas, retinoblastoma, Ewing's sarcoma, neuroblastoma, osteosarcoma, hemangioma, leukemias, and neoplastic diseases of the bone marrow involving excessive proliferation of white blood cells. Due to the association between angiogenesis and various disease conditions, substances that have the ability to modulate angiogenesis would be potentially useful treatments for these disease conditions.

Excessive angiogenesis also can occur during healing at the site of a surgical incision or other tissue trauma, and can result in scarring. Agents with the ability to modulate angiogenesis therefore also would be potentially useful in treatments to prevent scarring.

The invention provides methods for identifying a substance that (1) is a syndecan-modulating agent, and (2) alters the typical pattern, course, or extent of angiogenesis in a healthy or diseased tissue, organ, or organism. A syndecan-modulating agent that also alters the typical pattern, course, or extent of angiogenesis is herein referred to as an "angiogenesis-modulating agent." An angiogenesis-modulating agent can decrease angiogenesis in a localized tissue or organ, for example in a solid tumor or at the site of a surgical incision. An angiogenesis-modulating agent also can decrease angiogenesis in a systemic fashion and in some cases, to the extent that no vasculature development occurs. For example, a developing zebrafish embryo exposed to an angiogenesis-modulating agent may be devoid of vasculature. Non-limiting examples of angiogenesis-modulating agents that can decrease angiogenesis include polynucleotide analogues directed at ec2 nucleic acids and antibodies against EC2. Truncated forms of syndecan polypeptides also can be used as angiogenesis-modulating agents.

Angiogenesis-modulating agents also can promote or increase angiogenesis in particular situations. For example, it may be desirable to promote angiogenesis at the site of a surgical incision or other tissue trauma (e.g., at the site of a diabetic skin ulcer). Angiogenesis modulating agents that promote angiogenesis can be, for example, syndecan polypeptides or nucleic acid molecules encoding syndecan polypeptides.

The present invention provides pharmaceutical compositions and formulations that include one or more angiogenesis-modulating agents of the invention. Pharmaceutical compositions containing angiogenesis-modulating agents can be applied topically (e.g., to surgical incisions or diabetic skin ulcers). Formulations for topical administration of angiogenesis-modulating agents include, for example, sterile and non-sterile aqueous solutions, non-aqueous solutions in common solvents such as alcohols, or solutions in liquid or solid oil bases. Such solutions also can contain buffers, diluents and other suitable additives. Formulations for topical administration can include transdermal patches, ointments, lotions, creams, gels, drops, suppositories, sprays, liquids, and powders. Coated condoms, gloves and the like also may be useful. Conventional pharmaceutical carriers, aqueous, powder or oily bases, thickeners and the like may be necessary or desirable. Alternatively, pharmaceutical compositions containing angiogenesis-modulating agents can be administered orally or by injection (e.g., by subcutaneous, intradermal, intraperitoneal, or intravenous injection).

To identify angiogenesis-modulating agents, an animal can be contacted with a syndecan-modulating agent and monitored for any alteration or abnormalities in angiogenesis as compared to a control animal that has not received the syndecan-modulating agent. Angiogenesis can be monitored by, for example, microangiography (see Example 7, below). The animal can be any vertebrate animal such as a fish, a mouse, a rabbit, a guinea pig, a pig, or a monkey. The animal can be an embryo, a juvenile animal, or an adult.

The invention also provides methods for using an angiogenesis-modulating agent to modulate angiogenesis. For example, an angiogenesis-modulating agent can be administered to a vertebrate (e.g., a zebrafish, a mouse, a rat, or a human) such that the level of angiogenesis is altered from what it would be without the angiogenesis-modulating agent. In some embodiments, the angiogenesis-modulating agent is administered in an amount effective to reduce angiogenesis. As used herein, a "reduction" in the level of angiogenesis in a vertebrate treated with an angiogenesis-modulating agent refers to any decrease (e.g., a 1% decrease, a 5% decrease, a 10% decrease, a 25% decrease, a 50% decrease, a 75% decrease, a 90% decrease, or a 100% decrease) in the level of angiogenesis in the treated vertebrate as compared to the level of angiogenesis in an untreated vertebrate. For example, an antisense polynucleotide analog such as a morpholino directed against syndecan-2 can be administered to a vertebrate in order to reduce the level of angiogenesis (see, e.g., Example 7, below). Alternatively, more than one angiogenesis-modulating agents can be administered to a vertebrate to reduce angiogenesis. For example, a morpholino targeted to syndecan-2 and a morpholino targeted to another nucleic acid (e.g., a nucleic acid encoding vascular endothelial growth factor, or VEGF) can be administered simultaneously or sequentially to a vertebrate to reduce the level angiogenesis in a vertebrate (see, e.g., Example 7).

A truncated form of a syndecan (e.g., a cytoplasmically truncated form of a syndecan, such as the $\delta$S2 form of Syndecan-2) also can be administered to a vertebrate to reduce the level of angiogenesis. In some embodiments, one or more angiogenesis-modulating agents can be administered directly to a tumor or a tumor cell in a vertebrate (e.g., a breast tumor, a lung tumor, or a prostate tumor). Such administration can result in decreased angiogenesis in the tumor, and can kill the tumor cell or prevent or reduce growth of the tumor. The truncated form of syndecan can be administered in polypeptide form. Alternatively, a vertebrate or a tumor can be contacted with a nucleic acid containing a sequence that encodes the truncated form of the syndecan, such that the coding sequence is expressed to produce the truncated syndecan. Methods of the invention also can include monitoring the size of the tumor, before and/or after administration of the truncated syndecan.

In other embodiments, the angiogenesis-modulating agent can increase angiogenesis. As used herein, an "increase" in the level of angiogenesis in a vertebrate treated with an angiogenesis-modulating agent refers to any increase (e.g., a 1% increase, a 5% increase, a 10% increase, a 25% increase, a 50% increase, a 75% increase, a 90% increase, a 100% increase, or more than a 100% increase) in the level of angiogenesis in the treated vertebrate as compared to the level of angiogenesis in an untreated vertebrate. For example, a functional syndecan-2 polypeptide or a nucleic acid encoding a functional syndecan-2 polypeptide can be administered to a vertebrate to increase angiogenesis.

7. Diagnostic and Prognostic Applications

The invention also provides methods for using syndecan probes to detect syndecan expression in a cell preparation or in a particular tissue. For example, a technique such as in situ hybridization with a syndecan-2 nucleic acid probe can be used to detect syndecan-2 mRNA in a tissue (e.g., a tumor tissue; see Example 13, below). Such probes can be labeled with a variety of markers, including radioactive, chemiluminescent, or fluorescent markers, for example. Alternatively, an immunohistochemistry technique with an anti-syndecan-2 antibody can be used to detect syndecan-2 protein in a cell or a tissue. As syndecan-2 has been implicated in angiogenesis and vasculogenesis, the level of syndecan-2 mRNA or protein expression could serve as a diagnostic or prognostic indicator of cancer. For example, a tumor tissue exhibiting a higher level of syndecan-2 expression may have a more developed vasculature, and thus may be more likely to metastasize than a tumor tissue with less syndecan-2 expression.

The invention will be further described in the following examples, which do not limit the scope of the invention described in the claims.

EXAMPLES

Example 1

Identification of a Zebrafish Gene, ec2, Encoding a Syndecan-2 Homologue

Using BLAST analysis, a clone containing a coding sequence with strong similarity to mouse and human syndecan-2 was identified in a zebrafish EST database (GenBank accession number AI558535). The coding sequence, corresponding to a zebrafish syndecan-2 gene, was named ec2.

To obtain the full-length zebrafish ec2 coding sequence, automatic sequencing reactions were performed using primers based on the partial sequence reported in the EST database. The primers used to obtain the complete ec2 cDNA sequence were 5'-GAAGATCTCACCATGAGGAAC-CTTTGGATGAT-3' (SEQ ID NO:7), and 5'-GAAGATCTT-TATGCGTAAAACTCCTTGG-3' (SEQ ID NO:8).

The full-length sequence of the zebrafish ec2 open reading frame, together with the 5'-UTR, is shown in FIG. 1 (SEQ ID NO:1). The polypeptide sequence of zebrafish EC2 (SEQ ID NO:2; FIG. 2) has 48% to 50% sequence identity with human and mouse syndecan-2, as determined by clustal alignment using the GeneWorks v. 2.5.1 software. The alignment of zebrafish EC2 with mouse, rat, human, and Xenopus syndecan-2 is shown in FIG. 3.

Example 2

Zebrafish Care and Egg Collection

Standard zebrafish care protocols are described in Westerfield (2000) *The zebrafish book: A guide for the laboratory use of zebrafish (Danio rerio)*, 4$^{th}$ ed., University of Oregon Press, Eugene.

Zebrafish were kept in 6.5 gallon (26 liter) and 20 gallon (76 liter) plastic tanks at 28° C. Tanks with a 6.5 gallon capacity housed 25 fish, while 20 gallon tanks housed 70 fish. Tank water was constantly changed with carbon-filtered, UV-sterilized tap water (system water) at a rate of 15 to 40 mL/min, or was replaced each day by siphoning debris from the bottom of the tank. Tap water that had aged at least one day in an open (heated) tank to release chlorine was adequate, although more consistent conditions were obtained by adding commercial sea salts to deionized or distilled water (60 mg of Instant Ocean® salt per liter of water; see Westerfield, supra). A 10-hour dark and 14-hour light day cycle was maintained in the zebrafish facility.

Fish were fed brine shrimp twice a day. To make shrimp, 100 mL of brine shrimp eggs were added to 18 L of salt water (400 mL of Instant Ocean® salt per 18 L of water) and aerated vigorously. After 2 days at 28° C., the shrimp were filtered through a fine net, washed with system water, suspended in system water, and fed to fish. Alternatively, fish could also be fed with 'Tetra' brand dry flake food.

Zebrafish spawning was induced every morning shortly after the start of the light cycle. To collect the eggs, a 'false bottom container' system was used (Westerfield, supra). The system consisted of two containers of approximately 1.5 L, one slightly smaller than the other. The bottom of the smaller container was replaced with a stainless steel mesh having holes bigger than the diameter of zebrafish eggs. The smaller container was placed into the bigger container, and the setup was filled with system water. Up to eight zebrafish were placed inside the smaller container. When the fish spawned, the eggs fell through the mesh into the bigger container and thus could not be reached by the fish and eaten. About 10-15 minutes were allowed for spawning, after which time the smaller container with the fish was transferred into a second bigger container. Eggs were collected by filtering the remaining contents of the first bigger container through a mesh having holes smaller than the diameter of the eggs. Fish were used for spawning once a week for optimal embryo production.

Example 3

Spatial Expression Pattern of ec2 in Early Zebrafish Embryos

In situ hybridization was performed to determine the expression pattern of ec2 during zebrafish embryo development. The zebrafish ec2 coding region and 5'-UTR was labeled with digoxigenin-UTP (Roche Diagnostics, Indianapolis, Ind.) and used as a probe. In situ hybridization was performed as described in Jowett et al. (Jowett et al. (1999) *Methods Cell Biol.* 59:63-85). The spatial expression pattern of ec2 was determined during late somitogenesis (20.5 hours post-fertilization), at the 26-somite stage (22 hours post-fertilization), at the 28-somite stage (23 hours post-fertilization), and at time points post-somitogenesis (27, 28, 33, and 48 hours post-fertilization). At 20.5 hours, ec2 expression was observed in the vascular mesenchyme, or cells surrounding the presumptive axial vessels. At the 26-somite stage, ec2 expression also was detected in the hypochord, a single cell-wide midline structure immediately ventral to the notochord and dorsal to the dorsal aorta. This expression pattern persisted through 33 hours post-fertilization but had disappeared by 48 hours, at which point ec2 expression was detected in the dorsal fin buds. Expression of ec2 also was detected throughout the head and the dorsal neural tube starting at about 22 hours post-fertilization, suggesting a possible function of EC2 in development of the central nervous system.

Example 4

Morpholino Inactivation of Zebrafish ec2

To determine the function of ec2 in early zebrafish development, morpholinos (MOs) targeting the 5'-UTR of zebrafish ec2 were generated and used to decrease EC2 production. The zebrafish ec2-MOs had the following sequences:

```
ec2-MO#1:
5'-GGTTCCTCATAATTCCTCAGTCTTC-3'    (SEQ ID NO:9)

ec2-MO#2:
5'-GCTCGTGAAAGCGGAAAATCGC-3'       (SEQ ID NO:10)

ec2-MO#3:
5'-CCTCAGTCTTCGCTCGTGAAAGCG-3'     (SEQ ID NO:11)
```

In addition, an ec2-MO with a 4-base mismatch to ec2-MO#1, designated ec2-MO (Δ4), was used to assess the specificity of ec2-MO targeting. ec2-MO (Δ4) had the following sequence: 5'-GGTaCCTgATAATaCCTCAcTCTTC-3' (SEQ ID NO:12). The mismatched bases are indicated by lowercase letters. As other negative controls, a nacre-MO (5'-CATGTTCAACTATGTGTTAGCTTCA-3', SEQ ID NO:13) and a UROD-MO (5'-GAATGAAACTGTCCT-TATCCATCA-3', SEQ ID NO:14) were generated.

Morpholinos were obtained from Gene Tools, L.L.C. (Philomath, Oreg.), and were designed to bind to the 5'-UTR at or near the initiating methionine. Sequences were selected based on parameters recommended by the manufacturer, such that morpholinos were 21 to 25 nucleotides in length and had 50% G/C and 50% A/T content. Internal hairpins and runs of four consecutive G nucleotides were avoided.

Morpholinos were solubilized in water at a concentration of 50 mg/mL. The resulting stock solution was diluted to working concentrations of 0.09 to 3 mg/mL in water or 1× Danieau solution. Danieau buffer consisted of 8 mM NaCl, 0.7 mM KCl, 0.4 mM $MgSO_4$, 0.6 mM $Ca(NO_3)_2$, and 5.0 mM HEPES (pH 7.6). Zebrafish embryos at the 1 to 4 cell stages were microinjected with 4-9 nL of morpholinos.

The morpholino injection method was very similar to the mRNA injection method described in Hyatt and Ekker (supra). The collected eggs were transferred onto agarose plates as described in Westerfield (supra). While agarose plates for mRNA injections were kept cold to slow embryo development, the plates for morpholino injections were prewarmed to approximately 20° C., since morpholino injection into cold embryos was found to increase non-specific effects and mortality of the injected embryos.

Needles used for morpholino injections were the same as for mRNA injections (Hyatt and Ekker, supra). The needles were back-filled with a pipette and calibrated by injecting the loaded morpholino solution into a glass capillary tube. The picoinjector volume control was then set up for 1.5 to 15 nL. The injection volume depended on the required dose; 1.5 ng to 18 ng of morpholino usually were injected. Morpholino solutions were injected through the chorion into the yolk of zebrafish embryos. Injected embryos were transferred to petri dishes containing system water and allowed to develop at 28° C. Typically, at least 80% of the embryos injected in each experiment survived and were used for subsequent experiments.

Example 5

Efficacy of Morpholino Targeting

To assess the efficacy of morpholino targeting of ec2, an ec2 5' untranslated region-green fluorescent protein (UTR-GFP) fusion construct was prepared with the ec2 5' UTR containing the ec2-MO#1 targeting sequence. PCR mutagenesis was used to amplify 5' ec2 sequences (primers 5'-GCAG-GATCCGCGATTTTCCGCTTTCACGA-3', SEQ ID NO:15; and 5'-ACCTGAATTCAGGTTCCTCATAATTC-CTCAG-3', SEQ ID NO:16) and GFP sequences (primers 5'-ACGTGAATTCGAGTAAAGGAGAAGAACTT-3', SEQ ID NO:17; and 5'-CAGTCTCGAGTTATTTGTATAGT-TCATCCATG-3', SEQ ID NO:18). The ec2 and GFP amplicons were digested with EcoRI/XhoI and BamHI/EcoRI, respectively, and subcloned into pCS2+ (Rupp et al. (1994) *Genes Dev.* 8:1311-1323; and Turner and Weintraub (1994) *Genes Dev.* 8:1434-1447) to generate the pCS2+ec2 5' UTR-GFP fusion construct.

The fusion construct was linearized with NotI. SP6 RNA polymerase (Ambion, Austin, Tex.) was used for in vitro synthesis of mRNA. Embryos were co-injected with mRNA synthesized from the fusion construct and ec2-MO#1 or the UROD MO as a negative control. GFP expression was assessed as previously described (Nasevicius and Ekker (2000) *Nat. Genet.* 26:216-220). Injection of embryos with both 7 ng ec2-MO#1 and the ec2 5' UTR-GFP RNA resulted in a drastic reduction in GFP expression as compared to the level of GFP expression in embryos injected only with the ec2 5' UTR-GFP RNA. In contrast, co-injection with the UROD MO resulted in strong GFP expression at a level comparable to that observed in embryos injected only with the ec2 5' UTR-GFP RNA.

Example 6

Morphology of Zebrafish Embryos Infected with ec2-MO

The phenotypes of zebrafish embryos injected with morpholinos were first assessed by visual inspection with a dissecting microscope. At about 24 hours post-fertilization, embryos began to exhibit varying extents of dorsal curvature. Approximately 7-8% of the embryos that survived after injection of 5 ng ec2-MO#1 or 6 nm ec2-MO#2 exhibited dorsal curvature at 24 hours post-fertilization (FIG. 4A). When ec2-MO#1 and ec2-MO#2 were injected together, slightly more than 40% of the surviving embryos had dorsal curvature. In separate studies, 50% of embryos injected with 8 ng ec2-MO#1 displayed dorsal curvature at 24 hours (n=63), as did 12% of embryos injected with 6 ng ec2-MO#2 (n=85) and 35% of embryos injected with 7.5 ng ec2-MO#3 (n=69; FIG. 4B). Injection with 8 ng of the 4-base mismatch morpholino, ec2-MO (Δ4), did not result in a curved phenotype in any 24 hour embryos. In addition to dorsal curvature, embryos injected with the ec2 morpholinos exhibited an enlarged pericardium, a lack of visible circulation, and defective head formation, possibly due to cell death in the brain.

Figure 5:
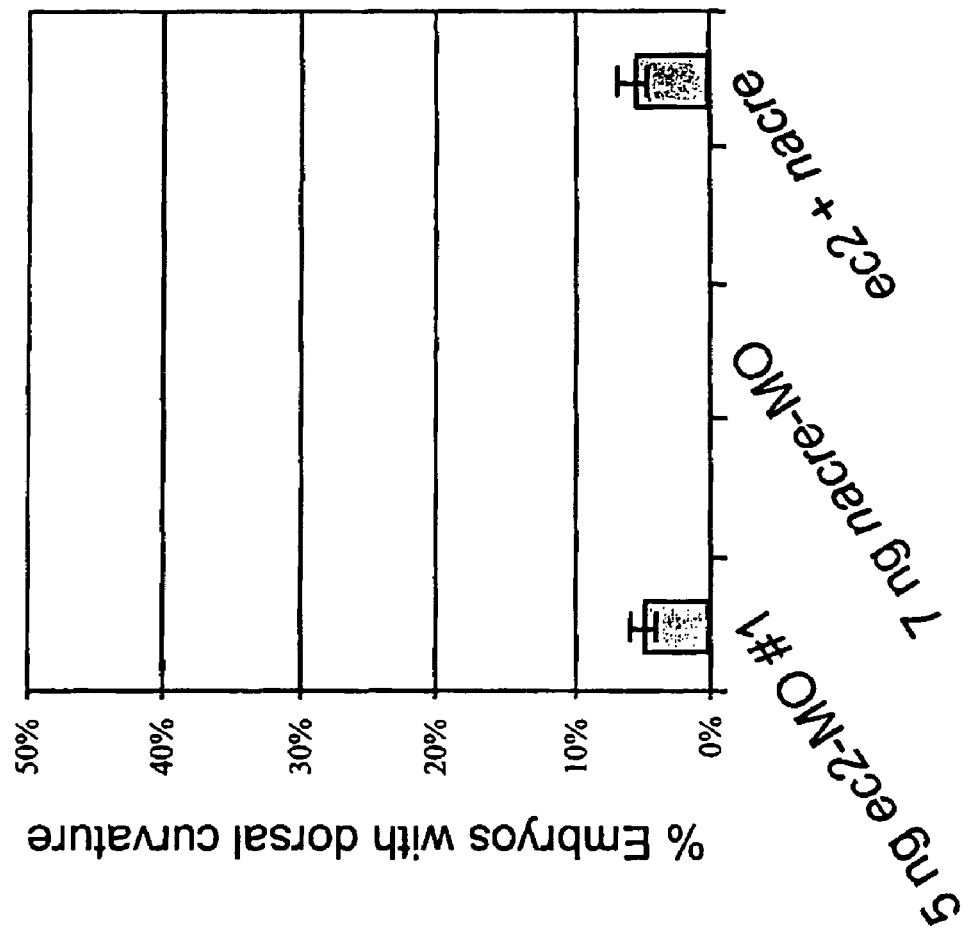
FIG. 5 is a graph showing the percentage of surviving embryos that exhibit dorsal curvature following injection with ec2 and/or nacre morpholinos.

The effect of the ec2 morpholinos was specific, as injection of either ec2-MO#1, ec2-MO#2, or ec2-MO#3 gave rise to the same phenotype while ec2-MO (Δ4) had no effect. Furthermore, injection with 7 ng of the nacre-MO did not result in any embryos with dorsal curvature (FIG. 5), and the nacre-MO did not synergize with ec2-MO#1 to increase the incidence of the curved phenotype above the level observed with ec2-MO#1 alone.

Figure 6:
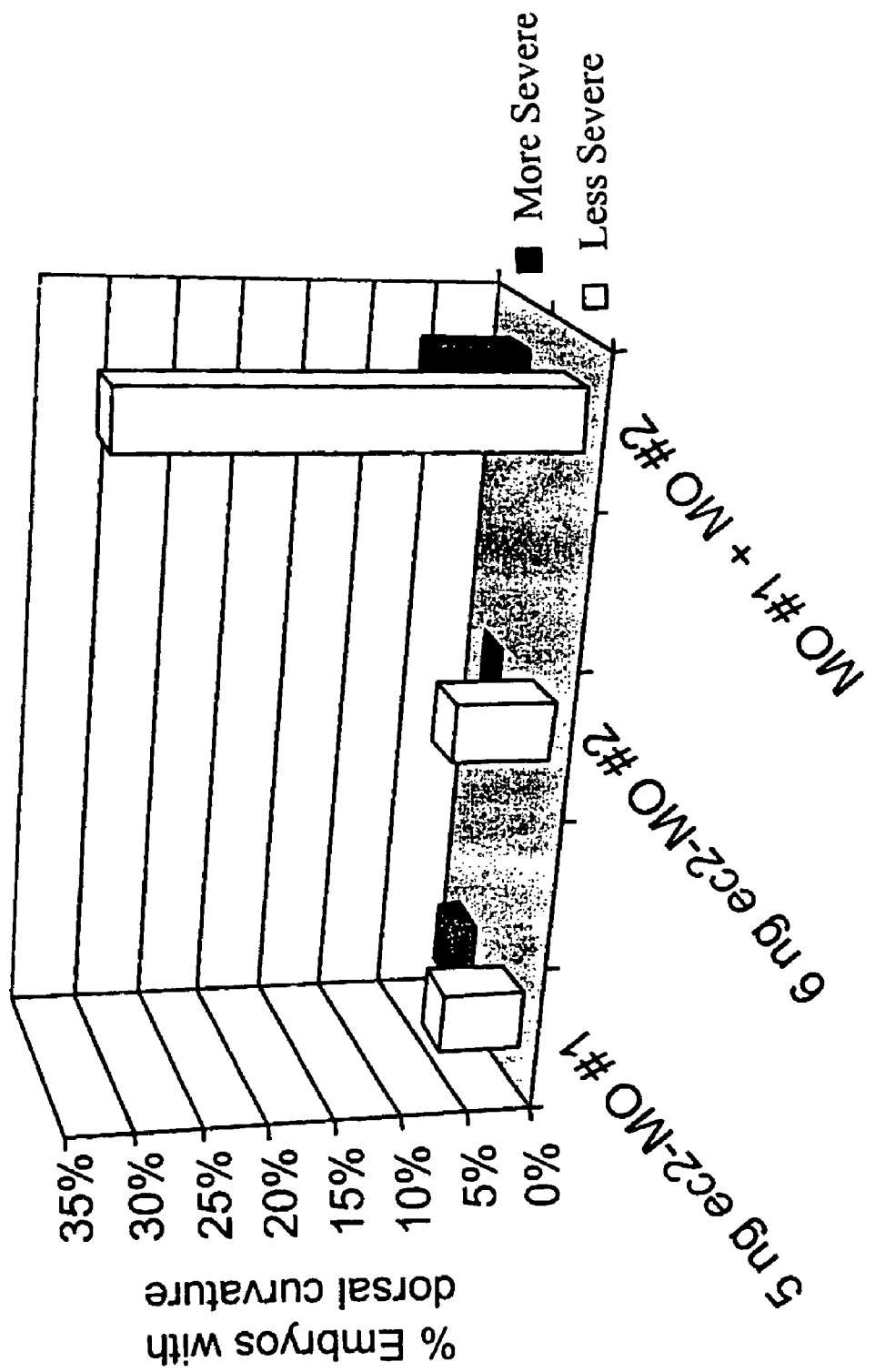
FIG. 6 is a three-dimensional column graph showing the percentage of surviving embryos that exhibit a less severe or more severe dorsal curvature phenotype following injection with ec2 morpholinos.

The appearance of the dorsal curvature in affected embryos ranged from a mild bend to a more extreme, U-shaped curve. Embryos exhibiting dorsal curvature thus were scored as having a less severe or a more severe phenotype. As depicted in FIG. 6, most surviving embryos with dorsal curvature after injection of either ec2-MO#1 or ec2-MO#2 displayed the less severe phenotype. Simultaneous injection of both ec2-MO#1 and ec2-MO#2 caused approximately 30% of the injected embryos to display the less severe phenotype and slightly more than 5% of the embryos to display the more severe phenotype. These morpholinos therefore act synergistically.

Example 7

Microangiography Analysis of Zebrafish Embryos Injected with ec2-MOs

Figure 7:
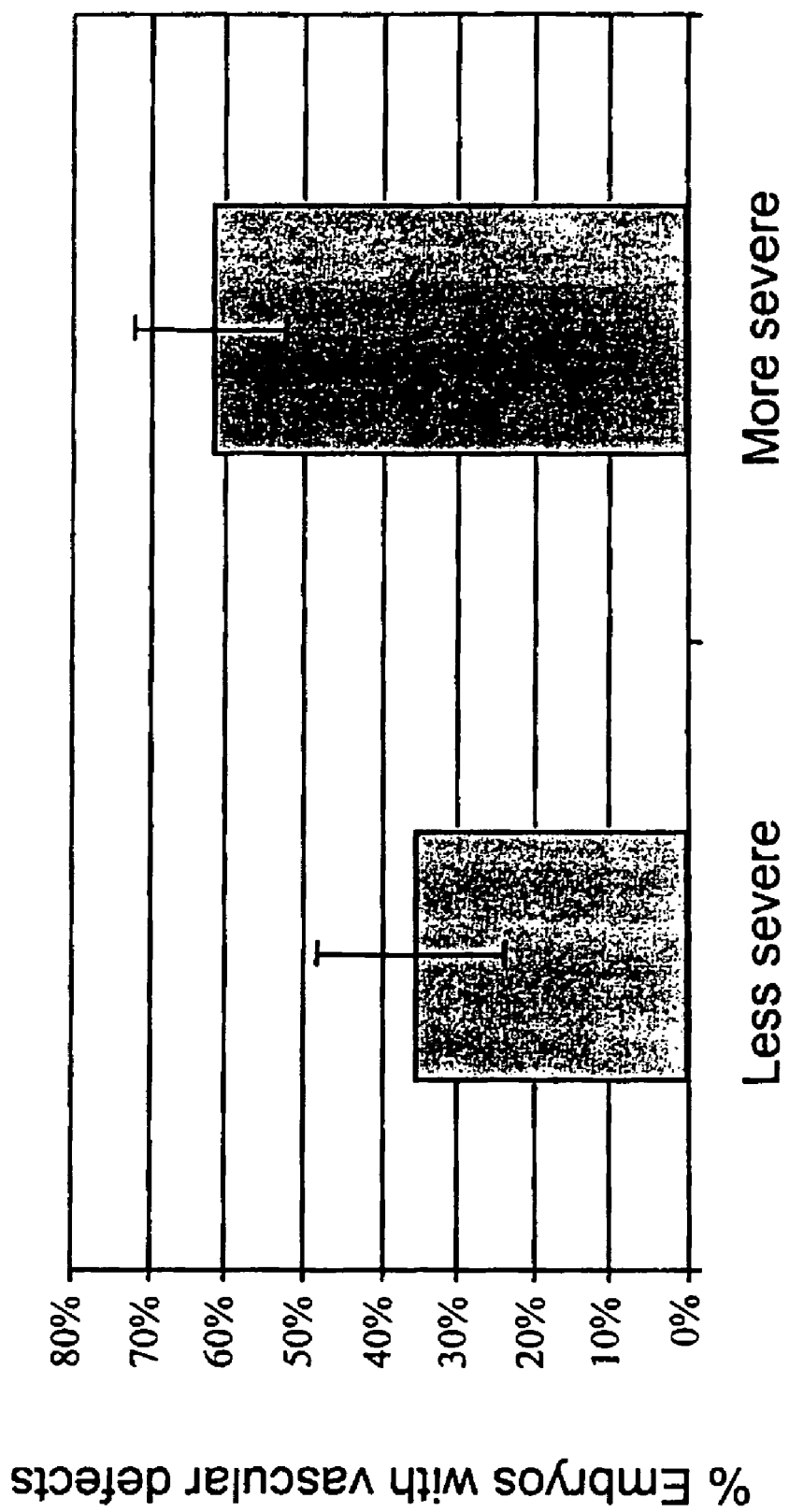
FIG. 7 is a graph showing the percentage of surviving embryos that exhibit defects in angiogenesis ("less severe") or vasculogenesis ("more severe") after injection of an ec2 morpholino.

To determine whether the vasculature in zebrafish embryos injected with ec2-MOs formed properly, microangiography was performed on both uninjected control embryos and embryos injected with ec2-MOs. Fluorescein isothiocyanate- (FITC-) Dextran dye was microinjected into the common cardinal vein of zebrafish embryos as described in Nasevicius et al. (2000) *Yeast* 17:294-301. Between 10-15 nL of FITC-Dextran fluorescent dye (1 µg/mL) was microinjected into 48 hour embryos incubating in 0.004% Tricain solution. The dye was taken to the heart and then pumped into the systemic circulation, allowing visualization of the entire vasculature by fluorescent microscopy. These studies revealed that nearly 100% of embryos injected with 8 ng ec2-MO#1 exhibited defects in angiogenesis (sprouting of new vessels from existing axial vessels) and/or vasculogenesis (initial formation of axial vessels). FIG. 7 shows the percentage of surviving injected embryos that exhibited a less severe phenotype vs. a more severe phenotype at 48 hours post-fertilization. Embryos with defective angiogenesis were scored as having a less severe phenotype, while those with defective vasculogenesis were scored as having a more severe phenotype. Between 25 and 31 surviving injected embryos were scored in each experiment. In the least severe cases, intersegmental vessels failed to form and the vascular plexus in the tail region failed to develop into a more complex network as seen or uninjected wild type embryos. In the most severe cases, no circulation was observed.

To further assess the nature of vascular defects in ec2-MO injected embryos, histological analysis was performed on those embryos showing no circulation upon microangiography analysis. Transverse sections were obtained from uninjected wild type embryos and from embryos injected with 8 ng ec2-MO#1 that showed no circulation. The sections were stained with hematoxylin and eosin. Compared to wild type embryos, the ec2-MO injected embryos exhibited a severely dilated dorsal aorta, suggesting that functional blood vessels had failed to form.

Figure 8:
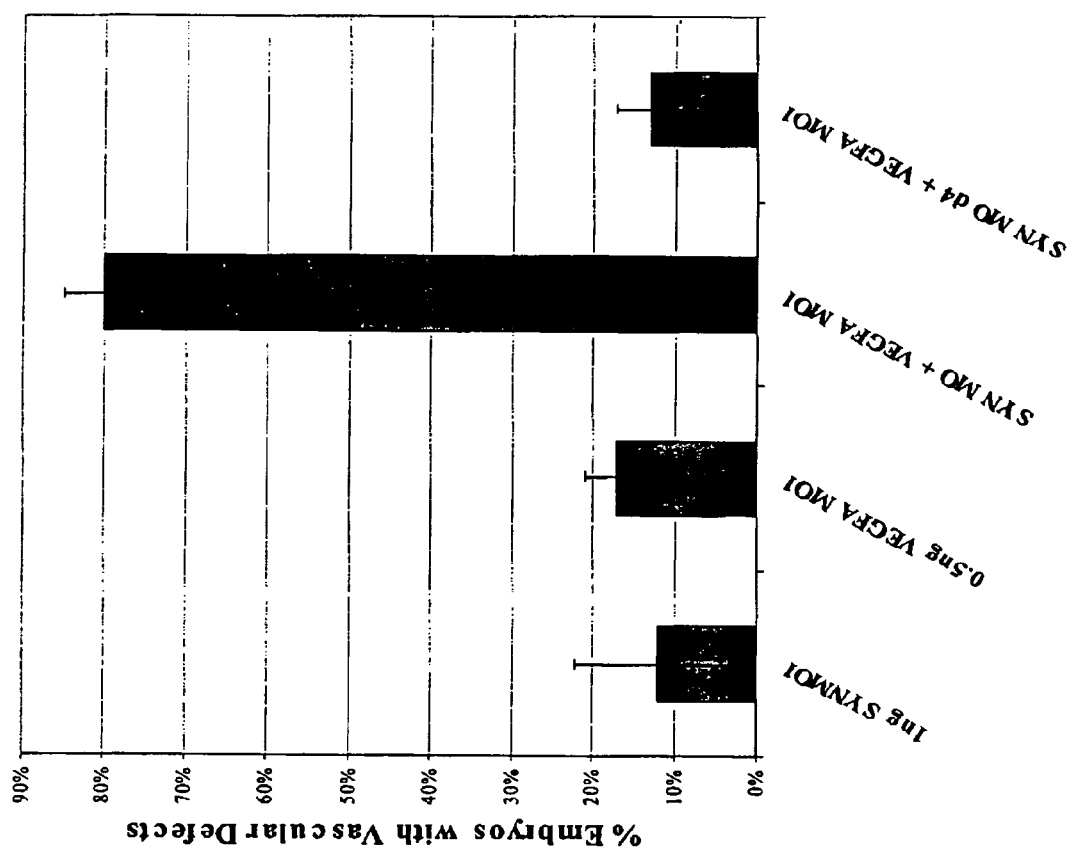
FIG. 8 is a graph showing the percentage of surviving embryos that exhibit vascular defects after injection with an ec2-MO and/or a VEGF MO.

In other experiments, MOs targeted to ec2 and VEGF were injected simultaneously. The VEGF-A MO#1 had the sequence 5'-GTATCAAATAAACAACCAAGTTCAT-3' (SEQ ID NO:19). Embryos were injected with 1 ng of ec2-MO#1 or 0.5 ng of VEGF-A MO#1 alone, or co-injected with 1 ng of ec2-MO#1 and 0.5 ng of VEGF-A MO#1 or 1 ng of ec2-MO (Δ4) and 0.5 ng of VEGF-A MO#1. Injected embryos were analyzed for vascular defects at 48 hours post-fertilization by microangiography. As shown in FIG. 8, a low dose of ec2-MO#1 and a low dose of VEGF-A MO#1 interacted synergistically in causing angiogenic defects in co-injected embryos. Microangiography revealed a weak defect in sprouting of intersegmental vessels in embryos injected with ec2-MO#1 alone, and a weak sprouting defect in the anterior trunk of embryos injected with VEGF-A MO#1 alone. Co-injected embryos exhibited more severe defects, such as aberrant sprouting of intersegmental vessels or even no sprouting of vessels in the trunk. No significant interaction between ec2-MO (Δ4) and VEGF-A MO#1 was observed.

Example 8

Expression of Early and Late Vascular Markers after Injection with ec2-MOs

In situ hybridization experiments were performed to assess the expression of vascular markers in embryos injected with ec2-MOs and in uninjected controls. Expression of the early vascular markers, fli-1 and flk-1, was examined at 24 hours post-fertilization, while expression of the late vascular markers, tie-1 and tie-2, was examined between 25 and 48 hours post-fertilization. Axial expression of both flk-1 and fli-1 was retained at 24 hours in both control and ec2-MO injected embryos, but intersegmental expression was absent in 76% of embryos injected with 8 ng ec2-MO#1 (n=24). This suggests that the process of angiogenic sprouting did not occur in the ec2-MO injected embryos. More specifically, 82% of the embryos injected with 8 ng ec2-MO#1 had reduced levels of fli-1 as compared to controls, while 75%±0% displayed reduced levels of flk-1.

To assess the integrity of vasculogenesis, ephrin-B2 and ephrin-B4 expression was analyzed in embryos injected with 8 ng ec2-MO#2. Ephrin-B2 and Ephrin-B4 are transmembrane ligands that mark arterial and venous endothelial cells, respectively (Wang et al. (1998) *Cell* 93:741-753). Expression of ephrin-B2 in the dorsal aorta was not affected in ec2-MO injected embryos. Expression of ephrin-B4 also was normal, suggesting that primary formation of the axial vessels was normal in ec2-MO injected embryos.

Intersegmental expression of tie-1 was reduced at about 25-26 hours in 68% of embryos injected with 8 ng ec2-MO#1 (n=27), as compared to uninjected controls. A reduction in axial expression was observed as early as 28 hours post-fertilization. 43%±3% of injected embryos showed lower levels of the tie-2 at 48 hours, as compared to uninjected embryos. Expression of tie-2 also was reduced at 28 hours in 62% of embryos injected with 8 ng ec2-MO#1, and remained reduced at 48 hours. Thus, EC2 may play an important role in stabilization and maintenance of mature vessels.

Example 9

Rescue of MO-induced Angiogenic Defects by Exogenous EC2 Protein

Experiments were conducted to determine whether the presence of exogenous zebrafish EC2 protein could rescue the angiogenic defect observed in ec2-MO injected embryos. An EC2 expression construct was prepared by using PCR to introduce EcoRI sites into the 5' and 3' ends of the zebrafish ec2 open reading frame. A plasmid containing the ec2 coding sequence was used as a template. The primers (with EcoRI sites at their 5' ends) were: 5'-CCGGAATTCCACCATGAG-GAACCTTTGGATGAT-3', SEQ ID NO:20; and 5'-CCG-GAATTCTTATGCGTAAAACTCCTTG-3', SEQ ID NO:21. The PCR fragment was subcloned into the EcoRI site of the FRM 2.1 expression vector (Gibbs et al. (2000) *Marine Biotechnology* 2:107-125).

Figure 9B:
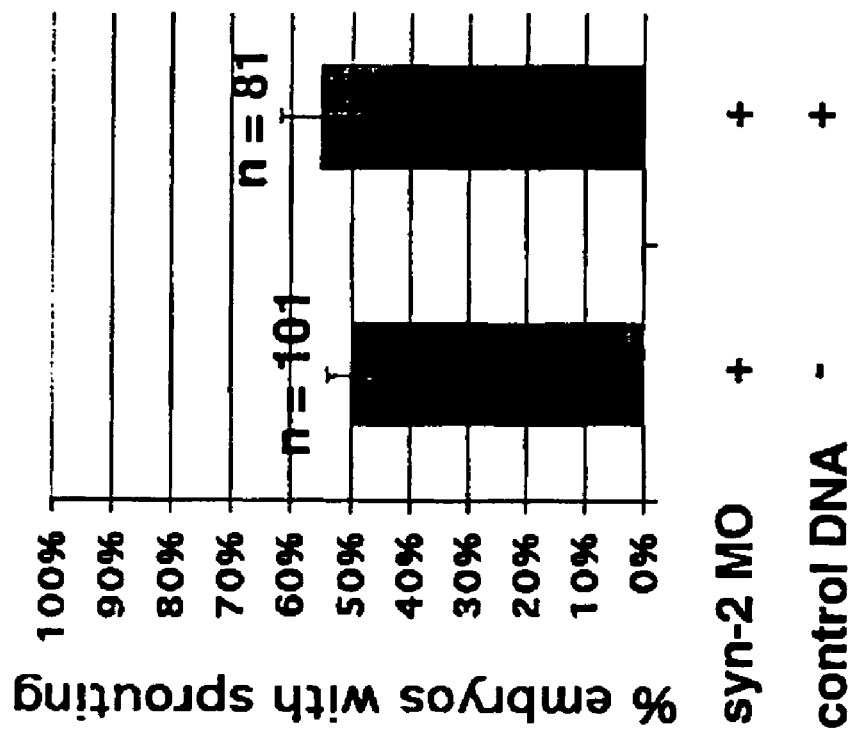
FIGS. 9A and 9B are graphs showing the percentage of surviving embryos that exhibit intersegmental expression of flk-1 after injection with an ec2-MO in combination with an ec2 expression construct or a control vector.
Figure 9A:
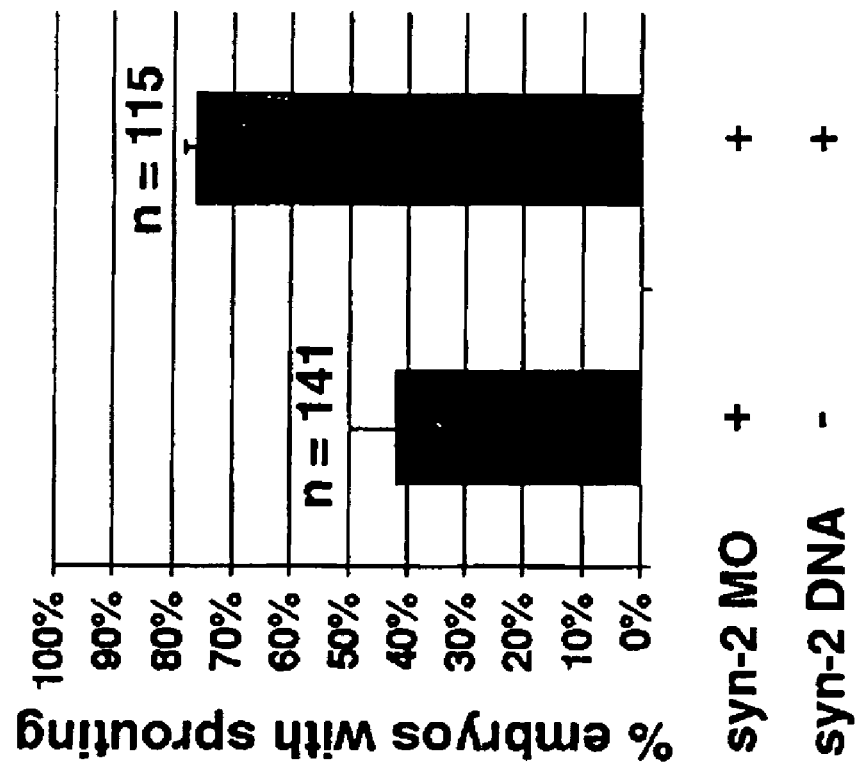

Embryos were injected with 7-8 ng of ec2-MO#3 and 3 pg of the EC2 expression construct, and a subset also was injected with a solution of the ec2 5' UTR-GFP fusion construct. GFP expression was used as a lineage tracer to facilitate the identification of successfully injected embryos. In situ analysis of flk-1 expression revealed that a significantly higher fraction of embryos co-injected with ec2-MO and ec2 DNA showed intersegmental vessels (FIG. 9A). In contrast, there was no significant difference in the fraction of embryos showing intersegmental expression of flk-1 in embryos co-injected with ec2-MO and the GFP expression construct compared to those injected with ec2-MO alone (FIG. 9B). These experiments indicated that the angiogenic defect observed in ec2-MO-injected embryos is specific to a loss of function of the endogenous ec2 gene.

Example 10

Forced Expression of Cytoplasmically-truncated EC2

To determine whether a cytoplasmically-truncated form of EC2, dS2, would have a deleterious effect on vascular development in zebrafish embryos, dS2 was overexpressed in embryos by injection of a dS2 expression construct. To generate this expression construct, a DNA fragment encoding a cytoplasmically truncated form of zebrafish EC2 was generated by PCR using plasmid DNA containing the ec2 coding sequence as a template. The primers (with EcoRI sites at their 5' ends) were 5'-CCGGAATTCCACCATGAGGAAC-CTTTGGATGAT-3' SEQ ID NO:20, and 5'-CCGGAAT-TCTTACGGTTTCCTCTCTCCCAG-3' (SEQ ID NO:22). The PCR fragment was subcloned into the EcoRI site of the FRM 2.1 expression vector.

Embryos were injected with either 9 pg GFP expression construct alone or a mixed solution of 8 pg δS2 and 1 pg GFP expression construct, and assessed for possible vascular defects by microangiography and molecular analyses. Forced expression of δS2 at lower doses did not affect morphology, but defective angiogenic sprouting in the trunk was observed upon microangiography analysis. In situ analysis of flk-1 expression indicated reduced sprouting in δS2-injected embryos, mimicking the effect of ec2-MO injections (FIG. 10A). In contrast, forced expression of EC2 and GFP did not have any significant effect on angiogenic sprouting. In other experiments, embryos were injected with 1 ng ec2-MO#3, 1.5 pg δS2 expression construct, 1.5 pg δS2 expression construct plus 1 ng ec2-MO#3, or 1.5 pg EC2 expression construct plus 1 ng ec2-MO#3. These studies revealed that a low dose of δS2 enhanced the effect of injecting a low dose of ec2-MO (FIG. 10B). Thus, forced expression of δS2 in embryos mimics the angiogenic defect observed in ec2-MO injected embryos, and support the anti-morphic function of δS2 in angiogenesis.

Example 11

The Vascular Function of Syndecan-2 is Conserved

Both zebrafish and mouse syndecan-2 are embryonically expressed in mesenchymal cells surrounding the axial vessels, suggesting that the vascular function of syndecan-2 is conserved. The functional conservation of syndecan-2 was tested in vascular development by assessing whether human syndecan-2 proteins could rescue the angiogenic defect in ec2-MO injected embryos. To prepare a human syndecan-2 expression construct, the open reading frame was amplified from a human fetal liver cDNA library (Genemed Biotechnologies, Inc.) using the following primers: 5'-ATGCG-GCGCGCGTGGATC-3' (SEQ ID NO:23), and 5'-TTACG-CATAAAACTCCTTAGTAG-3' (SEQ ID NO:24). The primers were designed based on the human syndecan sequence found in GenBank Accession No. XM_040582. EcoRI sites were introduced at the 5' and 3' ends of the coding sequence by another round of PCR. The PCR fragment was subsequently subcloned into the EcoRI site of the FRM expression construct.

Embryos were injected with 7-8 ng of ec2-MO#3 alone or in combination with the 4-5 pg of the human syndecan-2 expression construct. Intersegmental expression of flk-1 was analyzed in situ at 24 hours post-fertilization to assess the degree of angiogenic sprouting in the trunk. A significantly higher percentage of the group co-injected with the ec2-MO and human syndecan-2 DNA exhibited new sprouts, as compared to the group injected with ec2-MO alone (FIG. 11). In addition, a significantly higher fraction of embryos that were co-injected with ec2-MO and the human syndecan-2 expression construct showed intersegmental expression of flk-1, compared to those injected with ec2-MO only. The observation that human syndecan-2 protein alleviated the angiogenic defect observed in ec2-MO injected embryos suggests that the vascular function of syndecan-2 is conserved.

Example 12

Syndecan-2 Function in Vertebrates

Figure 12:
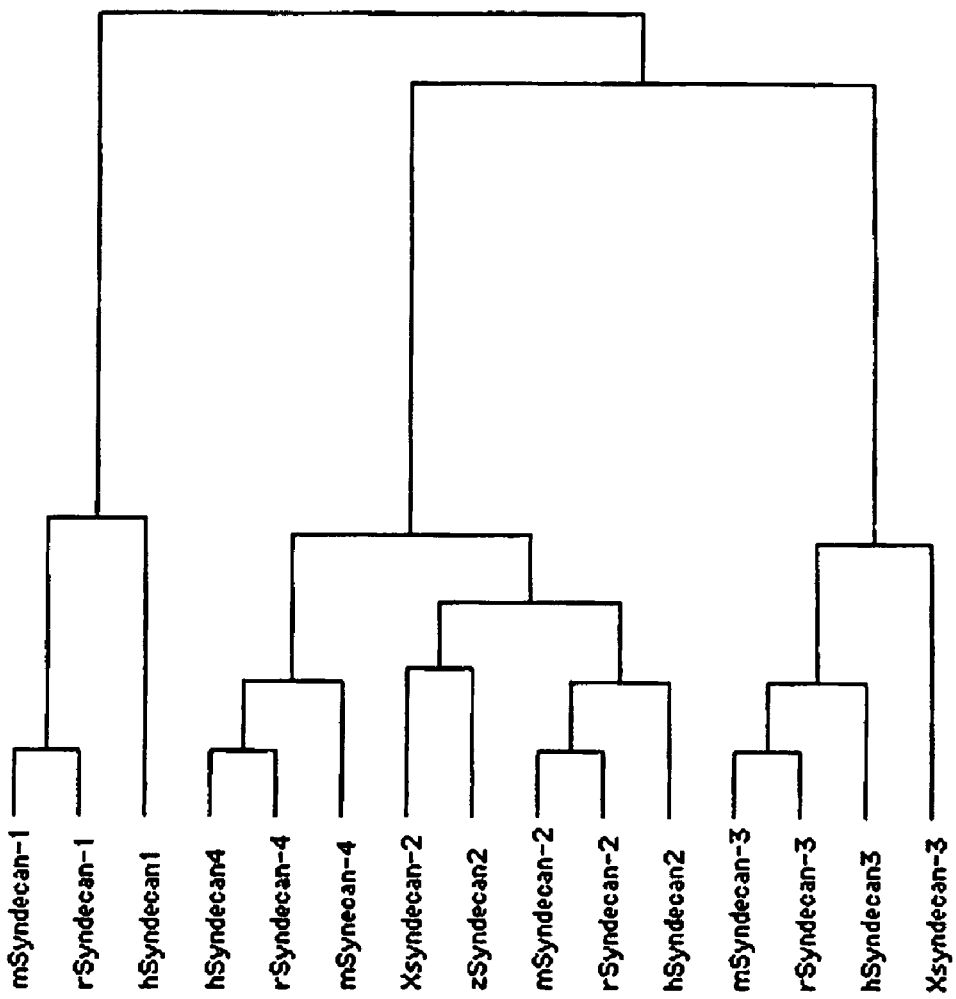
FIG. 12 is a homology tree showing clustering of zebrafish syndecan-2 to the vertebrate syndecan-2 family.

Based on amino acid sequence comparison, zebrafish EC2 uniquely clusters to the vertebrate syndecan-2 family (FIG. 12). To address whether syndecan-2 might perform similar vascular functions in other vertebrate organisms, expression of syndecan-2 was analyzed in mouse embryos at stages of development similar to those analyzed in zebrafish as described herein. On embryonic day 9.5, mouse syndecan-2 was expressed strongly in the head region and in the mesenchyme around axial vessels, similar to the expression pattern of ec2 in zebrafish embryos at 24 hours post-fertilization. This conservation of syndecan-2 expression in mouse suggests that syndecan-2 performs an essential vascular function during mammalian embryonic development.

Example 13

Expression of Human Syndecan-2 in Tumor Tissues

A survey of syndecan-2 expression was in various tumor tissues was performed using tissue spotted onto multi-tumor tissue microarray slides obtained from the Cooperative Human Tissue Network at National Cancer Institute (Bethesda, Md.). Tumor samples from eight tumor types (brain tumor, breast adenocarcinoma, colonic adenocarcinoma, lung cancer, lymphoma, melanoma, ovarian adenocarcinoma and prostate adenocarcinoma) were spotted on each slide. In situ hybridization was performed on the slides, using DIG-labelled human syndecan-2 RNA as a probe. A 390 bp fragment containing the partial human syndecan-2 coding sequence was amplified using the human syndecan-2 expression construct as the template. The primers used were 5'-AT-GCGGCGCGCGTGGATC-3' (SEQ ID NO:23), and 5'-CATTTGTACCTCTTCGGCTG-3' (SEQ ID NO:25). The PCR fragment was subcloned into the TOPO vector (Invitrogen, Carlsbad, Calif.). The plasmid DNA was linearized with NotI, and T3 RNA polymerase was used for in vitro synthesis of a DIG-labelled anti-sense probe. Tumor slides were dehydrated through a 100-90-70-30 ethanol series, 10 minutes each. In situ hybridization was performed using a protocol provided by the Chuang lab website ("baygenomics" dot "ucsf" dot "edu" slash "protocols").

Syndecan-2 expression was detected in 15 samples representing breast adenocarcinoma, lung squamous carcinoma and prostate adenocarcinoma tumor types. Positive staining was observed in and around tumor blood vessels in some of those samples. Expression of syndecan-2 in selective tumor tissue vasculature strongly suggests its potential function in tumorigenesis as an angiogenic agent.

Example 14

Effects of δS2 on VEGF-induced Angiogenesis

An FRM expression vector encoding LS2 was generated using the following primers: 5'-ATGAGGAACCTTTGGAT-GAT-3' (SEQ ID NO:26) and 5'-TTACGGTTTCCTCTCTC-CCTA-3' (SEQ ID NO:27). A DNA fragment containing the VLGF-165 open reading frame was isolated from the CS2+–VEGF-165plasmid (Ruowen Ge) by EcoRI restriction digest. The purified DNA fragment was subcloned into the EcoRI site of the FRM expression construct. The test DNA constructs (5 pg of the VEGF-165 construct alone, or 5 pg of the VEGF-165 construct with 2 pg of the LS2 construct) were mixed with an FRM-enhanced GFP (EGFP) expression construct. The mixtures were injected into 1-cell embryos at the interface between the yolk and the blastomere to ensure uniform mosaic distribution. Embryos showing GFP expression were selected prior to fixation for subsequent in situ analysis.

Figure 13:
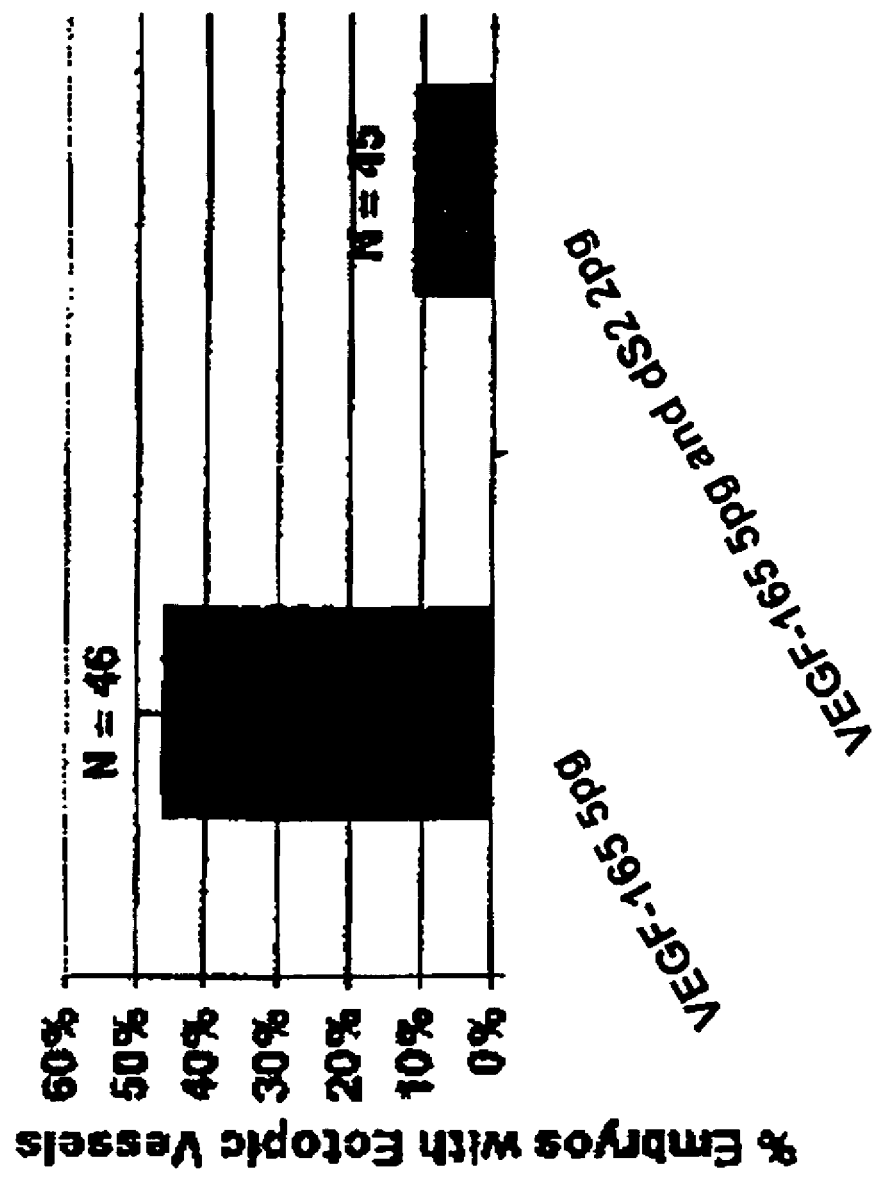
FIG. 13 is a graph showing the percentages of zebrafish embryos with ectopic vessels after injection of a VEGF-165 expression construct alone or in combination with an expression vector encoding a truncated form of Syndecan-2 ($\delta$S2).

Microangiography analysis as described in Example 7 revealed that nearly 50% of the embryos injected with the VEGF-165 expression construct alone had ectopic vessels (FIG. 13). Co-injection with the δS2 expression construct significantly decreased the occurrence of ectopic vessels. Thus, the dominant negative Syndecan-2 was able to inhibit VEGF-induced activation of angiogenesis.

Example 15

Effects of δS2 on Tumors Derived from LCC6 Breast Cancer Cells

Cell culture: Breast cancer-derived LCC6 cells (Doug Yee, University of Minnesota) were cultured in high glucose DMEM (Gibco/Invitrogen, Carlsbad, Calif.) supplemented with 10% FBS and 1% penicillin/streptomycin (Gibco/Invitrogen).

Cloning of human syndecan-2 expression constructs: The DNA fragment containing the human syndecan-2 coding sequence was isolated from the FRM-syndecan-2 expression construct (Chen et al. (2004) *Blood* 103:1710-1719) by EcoRI digestion. The cytoplasmically truncated form of Syndecan-2 (δS2; amino acids 1-186) was amplified by PCR using the pT2caggs-syndecan-2 expression construct as the template and primers having the sequences set forth in SEQ ID NO:22 and SEQ ID NO:23, with a premature stop codon introduced at the 3' end. Each DNA fragment was subcloned into the EcoRI site of the pT2caggs plasmid (David Largaespada, University of Minnesota).

Transfection: LCC6 cells were co-transfected with the test plasmid (pT2caggs empty vector or pT2caggs-human syndecan-2 derivatives) and a marker plasmid (pT2-CMV-GFP), using the ExGen 500 (linear polyethylenimine based) transfection reagent (Fermentas). Cells were changed to selection media (200 ng/mL puromycin) two days after transfection. About 20 days later, individual stably transfected clones were selected for expansion. Expression of the transgene in stable clones was assessed using RT-PCR.

RT-PCR analysis: Total RNA was isolated from $1\times10^6$ cells. To assess expression of endogenous syndecan-2 in each cell line, the following primers were used: 5'-ACCTTGA-CAACAGCTCCATT-3' (SEQ ID NO:28) and 5'-AGACT-GTCTGAGTGT TTCTC-3' (SEQ ID NO:29). To assess expression of transgenic syndecan-2 derived mRNA, the following transgene-specific primers were used: 5'-TGAGAAACACTCAG ACAGTCT-3' (SEQ ID NO:30) and 5'-CTCAAGGGGCTTCATGATG-3' (SEQ ID NO:31). The reverse primer anneals to a 3' untranslated region downstream of the syndecan-2 derived transgene in the pT2caggs plasmid. Human GAPDH expression was used as loading control. Primers used were: 5'-CCACCCATGGCAAATTC-CATGGCA-3' (SEQ ID NO:32) and 5'-TCTAGACGGCAG-GTCAGGTCCACC-3' (SEQ ID NO:33).

Tumor inoculations: Female BALBIc homozygous (nu/nu) mice, 6-8 weeks of age were maintained in a pathogen-free environment. Animals were inoculated by subcutaneous injection with LCC6 ($2\times10^6$) cells.

Immunohistochemistry: Tumor samples were embedded in O.C.T. and snap frozen in preparation for cryosectioning. Immunohistochemical detection was performed on 5-10 pm sections, using primary antibody against PECAM-1 (R&D systems, BBA7, 1:1000-1:5000 of a 1 mglmL stock solution) and anti-mouse IgG (whole molecule) peroxidase conjugate (A9044, Sigma). Staining was visualized using the cell and tissue staining kit (HRPIDAB anti-mouse, CTS002) obtained from R&D systems (Minneapolis, Minn.).

Tumor volume and microvessel density determination: Tumor measurements were performed using microcalipers. Tumor volumes were estimated using the formula $\pi16\times$ (larger diameter)$\times$(small diameter)$^2$ weekly after initiation of treatment (Tomayko and Reynolds (1989) *Cancer Chemother. Pharmacol.* 24:148-154). The microvessel density was calculated as the average number of PECAM (CD-31)-stained microvessels within three microscopic fields containing the maximum number of discrete microvessels, usually at the tumor periphery (Vermeulen et al. (1996) *Eur. J Cancer* 32A:2474-2484).

Figure 14:
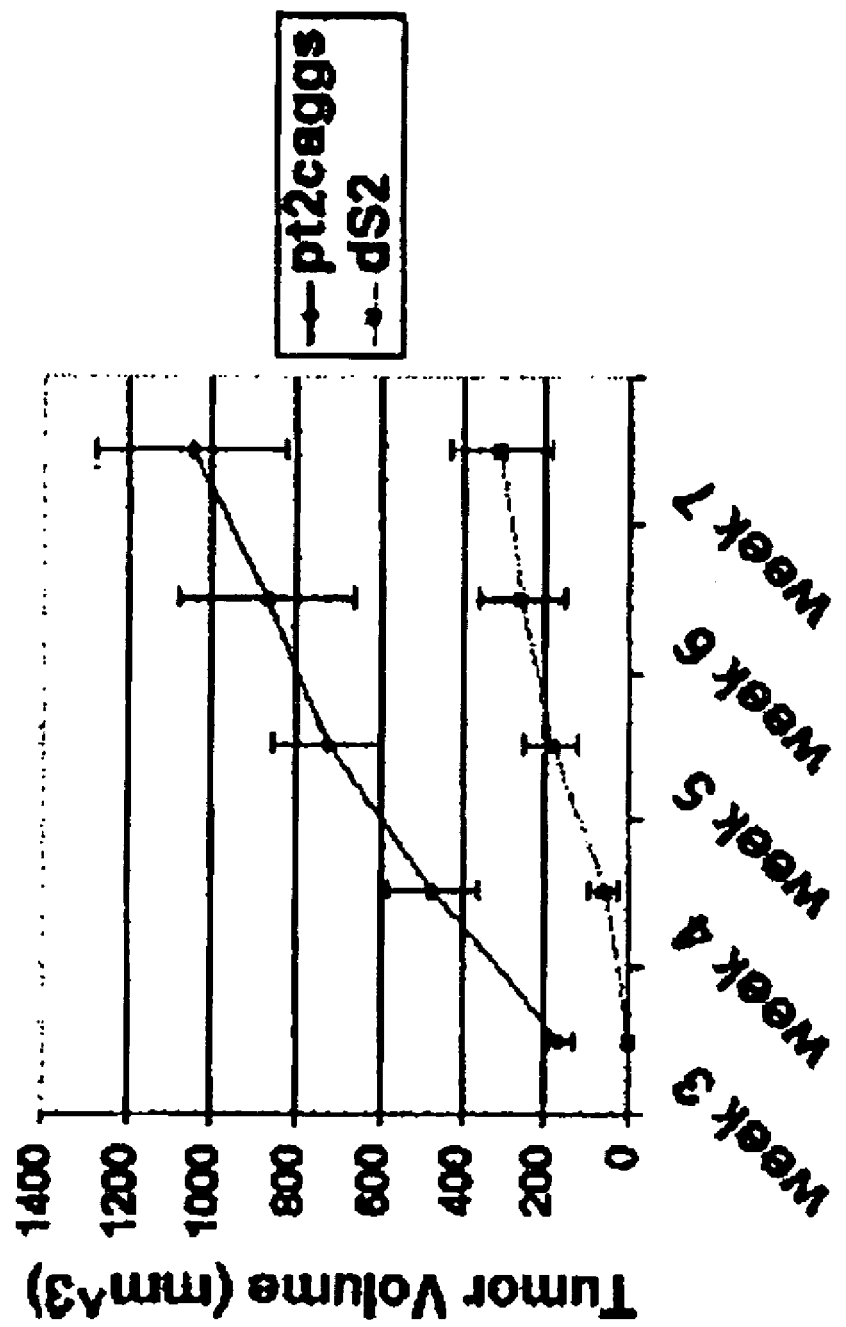
FIG. 14 is a graph showing growth of tumors derived from LCC6 breast cancer cells that were stably transfected with an expression vector encoding $\delta$S2 or vector control (pt2caggs) and inoculated into nude mice. Tumor volumes were measured at weekly intervals.

Results: To investigate the effect of δS2 on tumor growth, the pT2caggs-δS2 expression construct, along with the pT2caggs parental vector, were stably transfected into cells from the LCC6 breast tumor line. Transgene expression in the stable clones was confirmed by RT-PCR. A stable clone with δS2 transgene expression was expanded, and cells were subsequently inoculated into the flanks of athymic nude mice. Compared to the tumors from the control pT2caggs transfected cells, tumors from the δS2 stable clone were significantly smaller (FIG. 14, p=0.04).

Figure 15:
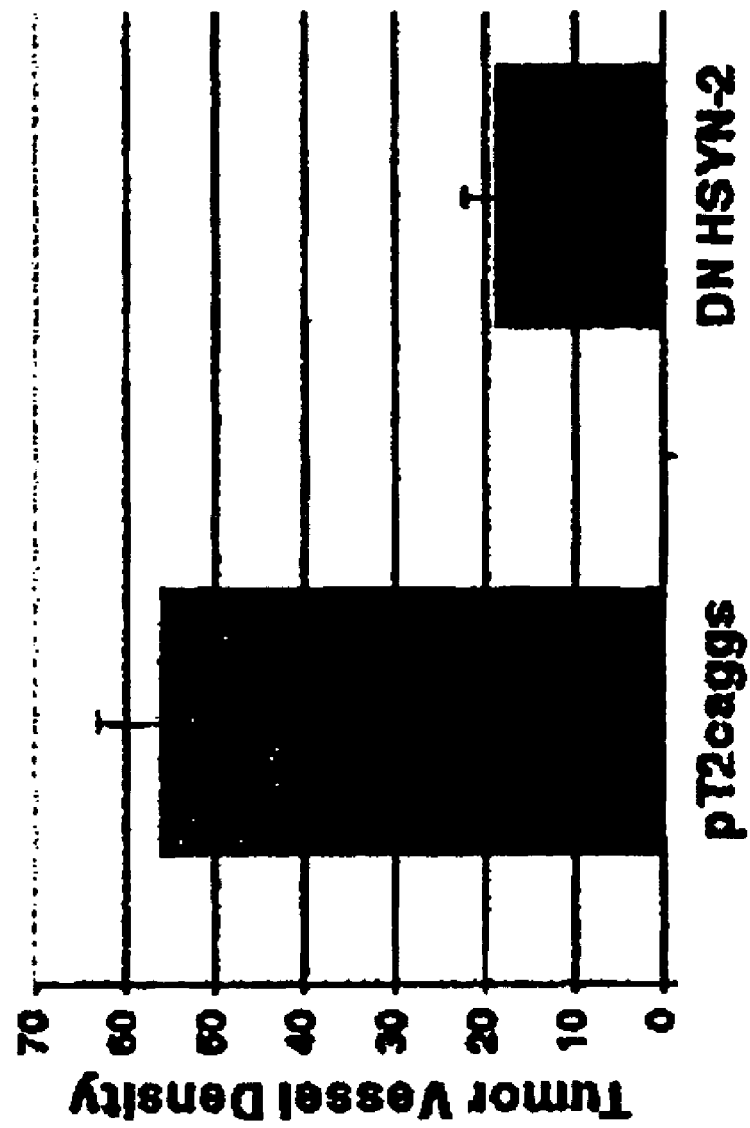
FIG. 15 is a graph showing tumor vessel density in tumors derived from LCC6 cells stably transfected with an expression vector encoding $\delta$S2 (DN HSYN-2) or vector control (pt2caggs).

To determine whether there might be a correlation between tumor growth and vessel density, anti-CD 31 (PECAM) immunohistochemical staining was performed, and vessel density was determined as described above. Compared to tumors derived from LCC6 cells transfected with the parental pT2caggs vector, tumors derived from cells transfected with δS2 showed lower vessel density (FIG. 15). These results indicate that slower tumor growth exhibited by δS2-transfected tumors correlates with less angiogenic activity.

Figure 16A:
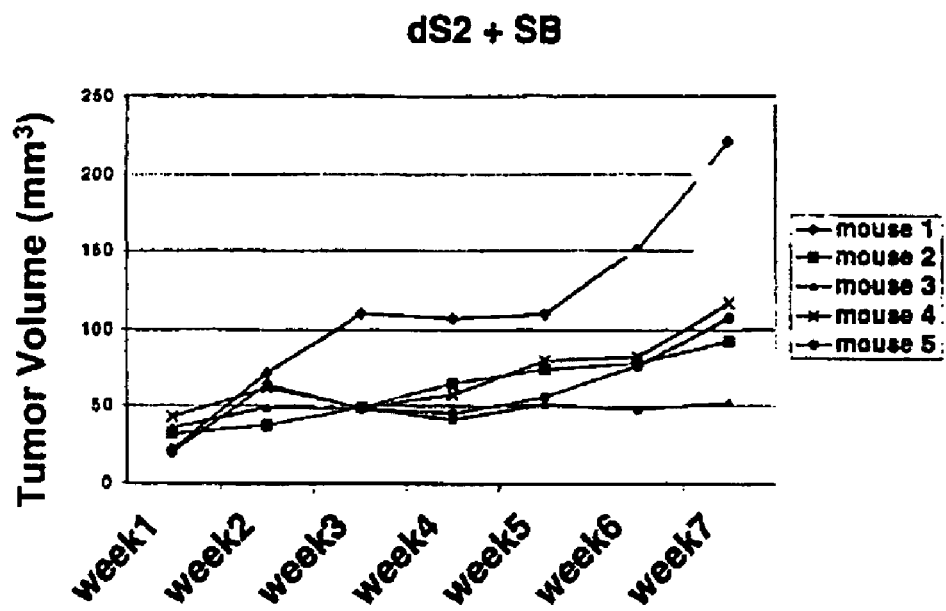
FIG. 16A is a graph showing tumor volumes in mice injected with LLC6 cells stably transfected with an expression vector encoding $\delta$S2.
Figure 16B:
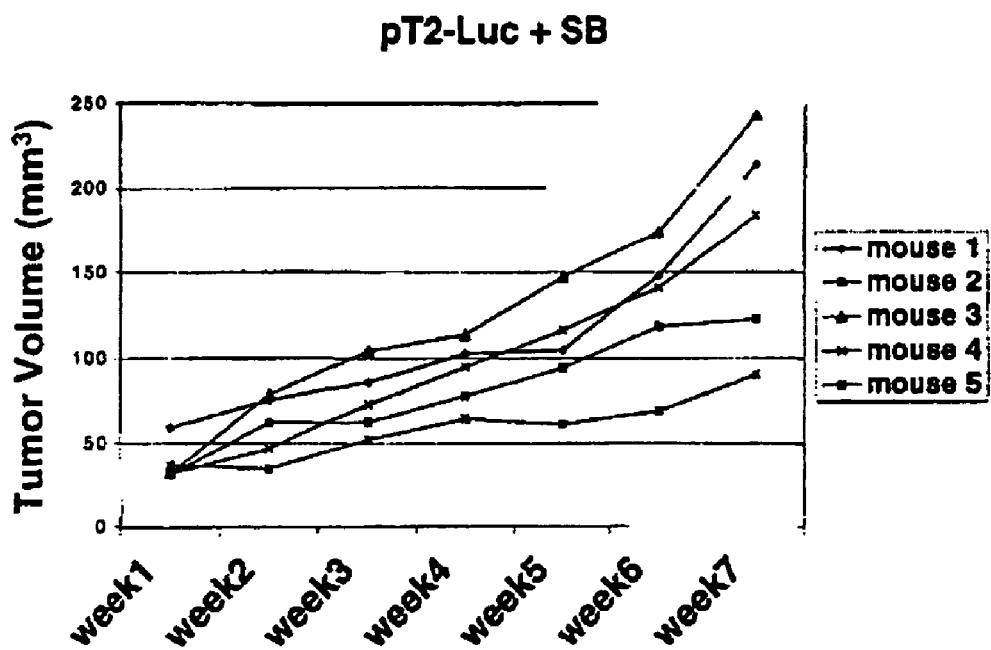
FIG. 16B is a graph showing tumor volumes in mice injected with LLC6 cells stably transfected with a pT2-Luc vector.

To determine the effect of δS2 on the growth of pre-established tumors, the Sleeping Beauty (SB) transposon-based system was used as an intratumoral gene transfer vector for breast tumor xenografts. This system has been demonstrated to be an effective gene transfer vector for glioblastoma xenografts (Ohlfest et al., in press). To assess whether SB-mediated gene transfer of δS2 would have a therapeutic effect on breast tumor growth, tumors were first established in female nude mice by subcutaneous inoculation with LCC6 tumor cells. SB and δS2 DNA cassettes were then introduced into pre-established tumors that were 4-6 mm diameter by injecting a solution containing SB and δS2 DNA: linear polyethylenimine (PEI) complexes. As controls, DNA cassettes containing SB and the luciferase reporter gene (pT2-Luc) were introduced into tumors in another group of nude mice. Tumor size was measured weekly post-injection. After 7 weeks, four of the five tumors injected with δS2 and SB were smaller compared to the tumors injected with pT2-Luc and SB (FIGS. 16A and 16B).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for reducing angiogenesis in a vertebrate in need thereof, said method comprising administering to said vertebrate a cytoplasmically truncated Syndecan-2 polypeptide, wherein said cytoplasmically truncated Syndecan-2 polypeptide is administered in an amount effective to reduce angiogenesis, and wherein angiogenesis is reduced in said vertebrate.

2. The method of claim 1, wherein said truncated Syndecan-2 polypeptide is a dominant negative Syndecan-2 polypeptide.

3. The method of claim 1, wherein said truncated Syndecan-2 polypeptide comprises amino acids 1 to 193 of the sequence set forth in SEQ ID NO: 2.

* * * * *

SEQUENCE LISTING

<160> NUMBER OF SEQ ID NOS: 33

<210> SEQ ID NO 1
<211> LENGTH: 691
<212> TYPE: DNA
<213> ORGANISM: Danio rerio

<400> SEQUENCE: 1

```
ccacgcgtcc gcccacgcgt ccgagacgcg attttccgct ttcacgagcg aagactgagg      60
aattatgagg aacctttgga tgattttaac cctcggcttg actgcctttc tctccggga     120 gcggatatca gtgtctgcgg ccaaatctcc ctccacgaca gatgacctgt acctggagga    180
ggctggatct ggaggatacc ctgaagatga tgatgatttc agctccggat cgggatcagg    240
agccggagag gttattgaag atcccgtcac agtaaacaca ctgttcttcg tgcctaaagc    300
agagcccacg caggactcca ccaaagactt cacaccgaaa gtggagacag tgacgtcaca    360
agacgccccc aaagactcga agaaacgcag gatagaggtt gcagttcccg tcacagaaga    420
ctctcgcaga aaccctgtca ccagcaccac cagcatccct cgacctccca tggatcccca    480
agacgtccag tcagaaaatc ttttccagag gacagaagtt ctggcagctg tgattgcagg    540
aggagtgatc ggcttcctct tcgccatctt cctcatcctc ctgctggttt accgcatgag    600
aaagaaggac gagggcagct acgatctggg agagaggaaa ccgtccggag cggcctatca    660
gaaagctccc accaaggagt tttacgcata a                                   691
```

<210> SEQ ID NO 2
<211> LENGTH: 208
<212> TYPE: PRT
<213> ORGANISM: Danio rerio

<400> SEQUENCE: 2

```
Met Arg Asn Leu Trp Met Ile Leu Thr Leu Gly Leu Thr Ala Phe Leu
 1               5                  10                  15

Ser Gly Glu Arg Ile Ser Val Ser Ala Ala Lys Ser Pro Ser Thr Thr
            20                  25                  30

Asp Leu Tyr Leu Glu Glu Ala Gly Ser Gly Tyr Pro Glu Asp
        35                  40                  45

Asp Asp Asp Phe Ser Ser Gly Ser Gly Ser Gly Ala Gly Glu Val Ile
    50                  55                  60

Glu Asp Pro Val Thr Val Asn Thr Leu Phe Phe Val Pro Lys Ala Glu
65                  70                  75                  80

Pro Thr Gln Asp Ser Thr Lys Asp Phe Thr Pro Lys Val Glu Thr Val
                85                  90                  95

Thr Ser Gln Asp Ala Pro Lys Asp Ser Lys Arg Arg Ile Glu Val
            100                 105                 110
```

```
Ala Val Pro Val Thr Glu Asp Ser Arg Arg Asn Pro Val Thr Ser Thr
            115                 120                 125

Thr Ser Ile Pro Arg Pro Met Asp Pro Gln Asp Val Gln Ser Glu
        130                 135                 140

Asn Leu Phe Gln Arg Thr Glu Val Leu Ala Ala Val Ile Ala Gly Gly
145                 150                 155                 160

Val Ile Gly Phe Leu Phe Ala Ile Phe Leu Ile Leu Leu Val Tyr
                165                 170                 175

Arg Met Arg Lys Lys Asp Glu Gly Ser Tyr Asp Leu Gly Glu Arg Lys
                180                 185                 190

Pro Ser Gly Ala Ala Tyr Gln Lys Ala Pro Thr Lys Glu Phe Tyr Ala
            195                 200                 205

<210> SEQ ID NO 3
<211> LENGTH: 202
<212> TYPE: PRT
<213> ORGANISM: Mus musculus

<400> SEQUENCE: 3

Met Gln Arg Ala Trp Ile Leu Leu Thr Leu Gly Leu Met Ala Cys Val
1               5                   10                  15

Ser Ala Glu Thr Arg Thr Glu Leu Thr Ser Asp Lys Asp Met Tyr Leu
                20                  25                  30

Asp Asn Ser Ser Ile Glu Glu Ala Ser Gly Val Tyr Pro Ile Asp Asp
            35                  40                  45

Asp Asp Tyr Ser Ser Ala Ser Gly Ser Gly Ala Asp Glu Asp Ile Glu
        50                  55                  60

Ser Pro Val Leu Thr Thr Ser Gln Leu Ile Pro Arg Ile Pro Leu Thr
65                  70                  75                  80

Ser Ala Ser Ser Pro Lys Val Glu Thr Met Thr Leu Lys Thr Gln Ser
                85                  90                  95

Ile Thr Pro Ala Gln Thr Glu Ser Pro Glu Glu Thr Asp Lys Glu Glu
            100                 105                 110

Val Asp Ile Ser Glu Ala Glu Lys Leu Gly Pro Ala Ile Lys Ser
            115                 120                 125

Thr Asp Val Tyr Thr Glu Lys His Ser Asp Asn Leu Phe Lys Arg Thr
        130                 135                 140

Glu Val Leu Ala Ala Val Ile Ala Gly Gly Val Ile Gly Phe Leu Phe
145                 150                 155                 160

Ala Ile Phe Leu Ile Leu Leu Val Tyr Arg Met Arg Lys Lys Asp
                165                 170                 175

Glu Gly Ser Tyr Asp Leu Gly Arg Lys Pro Ser Ser Ala Ala Tyr
            180                 185                 190

Gln Lys Ala Pro Thr Lys Glu Phe Tyr Ala
        195                 200

<210> SEQ ID NO 4
<211> LENGTH: 201
<212> TYPE: PRT
<213> ORGANISM: Rattus norvegicus

<400> SEQUENCE: 4

Met Gln Arg Ala Trp Ile Leu Leu Thr Leu Gly Leu Met Ala Cys Val
1               5                   10                  15

Ser Ala Glu Thr Arg Ala Glu Leu Thr Ser Asp Lys Asp Met Tyr Leu
                20                  25                  30
```

Asp Ser Ser Ser Ile Glu Glu Ala Ser Gly Leu Tyr Pro Ile Asp Asp
         35                  40                  45

Asp Asp Tyr Ser Ser Ala Ser Gly Ser Gly Ala Tyr Glu Asp Lys Gly
 50                  55                  60

Ser Pro Asp Leu Thr Thr Ser Gln Leu Ile Pro Arg Ile Ser Leu Thr
 65                  70                  75                  80

Ser Ala Ala Pro Glu Val Glu Thr Met Thr Leu Lys Thr Gln Ser Ile
                 85                  90                  95

Thr Pro Thr Gln Thr Glu Ser Pro Glu Glu Thr Asp Lys Lys Glu Phe
             100                 105                 110

Glu Ile Ser Glu Ala Glu Lys Gln Asp Pro Ala Val Lys Ser Thr
             115                 120                 125

Asp Val Tyr Thr Glu Lys His Ser Asp Asn Leu Phe Lys Arg Thr Glu
 130                 135                 140

Val Leu Ala Ala Val Ile Ala Gly Gly Val Ile Gly Phe Leu Phe Ala
145                 150                 155                 160

Ile Phe Leu Ile Leu Leu Leu Val Tyr Arg Met Arg Lys Lys Asp Glu
                 165                 170                 175

Gly Ser Tyr Asp Leu Gly Glu Arg Lys Pro Ser Ser Ala Ala Tyr Gln
             180                 185                 190

Lys Ala Pro Thr Lys Glu Phe Tyr Ala
             195                 200

<210> SEQ ID NO 5
<211> LENGTH: 201
<212> TYPE: PRT
<213> ORGANISM: Homo sapiens

<400> SEQUENCE: 5

Met Arg Arg Ala Trp Ile Leu Leu Thr Leu Gly Leu Val Ala Cys Val
 1               5                  10                  15

Ser Ala Glu Ser Arg Ala Glu Leu Thr Ser Asp Lys Asp Met Tyr Leu
                 20                  25                  30

Asp Asn Ser Ser Ile Glu Glu Ala Ser Gly Val Tyr Pro Ile Asp Asp
             35                  40                  45

Asp Asp Tyr Ala Ser Ala Ser Gly Ser Gly Ala Asp Glu Asp Val Glu
 50                  55                  60

Ser Pro Glu Leu Thr Thr Ser Arg Pro Leu Pro Lys Ile Leu Leu Thr
 65                  70                  75                  80

Ser Ala Ala Pro Lys Val Glu Thr Thr Thr Leu Asn Ile Gln Asn Lys
                 85                  90                  95

Ile Pro Ala Gln Thr Lys Ser Pro Glu Glu Thr Asp Lys Glu Lys Val
             100                 105                 110

His Leu Ser Asp Ser Glu Arg Lys Met Asp Pro Ala Glu Glu Asp Thr
             115                 120                 125

Asn Val Tyr Thr Glu Lys His Ser Asp Ser Leu Phe Lys Arg Thr Glu
 130                 135                 140

Val Leu Ala Ala Val Ile Ala Gly Gly Val Ile Gly Phe Leu Phe Ala
145                 150                 155                 160

Ile Phe Leu Ile Leu Leu Leu Val Tyr Arg Met Arg Lys Lys Asp Glu
                 165                 170                 175

Gly Ser Tyr Asp Leu Gly Glu Arg Lys Pro Ser Ser Ala Ala Tyr Gln
             180                 185                 190

Lys Ala Pro Thr Lys Glu Phe Tyr Ala

```
<210> SEQ ID NO 6
<211> LENGTH: 190
<212> TYPE: PRT
<213> ORGANISM: Xenopus laevis

<400> SEQUENCE: 6

Met Arg Asn Val Trp Leu Ile Val Pro Phe Ala Leu Leu Ala Ala Phe
 1               5                  10                  15

Ser Gly Glu Thr Trp Ala Gln Ala Asp Arg Asp Leu Tyr Ile Asp Ser
            20                  25                  30

Thr Glu Ser Ser Gly Asn Tyr Pro Val Asp Asp Asp Tyr Ser Ser
        35                  40                  45

Gly Ser Gly Ser Gly Ile Pro Ala His Asp Asp Glu Asp Asn Val
    50                  55                  60

Val Leu Thr Thr Val Gln Thr Leu Ile Ser Ser Pro Ser Ser Glu Met
65                  70                  75                  80

Pro Tyr Val Asp Thr Thr Thr Leu Lys Thr Gln Thr Lys Met Ala Pro
                85                  90                  95

Glu Thr Lys Glu Pro Gly Glu Val Glu Ser Thr Asn Thr Val Leu Val
            100                 105                 110

His Glu Asn Lys Asn Ile Ile Gln Thr Ala Thr His Thr Glu Asn Leu
        115                 120                 125

Phe His Arg Thr Glu Val Leu Ala Ala Val Ile Ala Gly Gly Gly Ile
    130                 135                 140

Gly Phe Leu Phe Ala Val Phe Leu Ile Leu Leu Val Tyr Arg Met
145                 150                 155                 160

Arg Lys Lys Asp Glu Gly Ser Tyr Asp Leu Gly Glu Lys Pro Ser
                165                 170                 175

Ser Ala Val Tyr Gln Lys Ala Pro Thr Lys Glu Phe Tyr Ala
            180                 185                 190

<210> SEQ ID NO 7
<211> LENGTH: 32
<212> TYPE: DNA
<213> ORGANISM: Artificial Sequence
<220> FEATURE:
<223> OTHER INFORMATION: primer

<400> SEQUENCE: 7
gaagatctca ccatgaggaa cctttggatg at                              32

<210> SEQ ID NO 8
<211> LENGTH: 28
<212> TYPE: DNA
<213> ORGANISM: Artificial Sequence
<220> FEATURE:
<223> OTHER INFORMATION: primer

<400> SEQUENCE: 8
gaagatcttt atgcgtaaaa ctccttgg                                   28

<210> SEQ ID NO 9
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 9
```
ggttcctcat aattcctcag tcttc                                          25

<210> SEQ ID NO 10
<211> LENGTH: 22
<212> TYPE: DNA
<213> ORGANISM: Artificial Sequence
<220> FEATURE:
<223> OTHER INFORMATION: antisense oligonucleotide

<400> SEQUENCE: 10
gctcgtgaaa gcggaaaatc gc                                             22

<210> SEQ ID NO 11
<211> LENGTH: 24
<212> TYPE: DNA
<213> ORGANISM: Artificial Sequence
<220> FEATURE:
<223> OTHER INFORMATION: antisense oligonucleotide

<400> SEQUENCE: 11
cctcagtctt cgctcgtgaa agcg                                           24

<210> SEQ ID NO 12
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 12
ggtacctgat aatacctcac tcttc                                          25

<210> SEQ ID NO 13
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 13
catgttcaac tatgtgttag cttca                                          25

<210> SEQ ID NO 14
<211> LENGTH: 24
<212> TYPE: DNA
<213> ORGANISM: Artificial Sequence
<220> FEATURE:
<223> OTHER INFORMATION: antisense oligonucleotide

<400> SEQUENCE: 14
gaatgaaact gtccttatcc atca                                           24

<210> SEQ ID NO 15
<211> LENGTH: 29
<212> TYPE: DNA
<213> ORGANISM: Artificial Sequence
<220> FEATURE:
<223> OTHER INFORMATION: primer

<400> SEQUENCE: 15
gcaggatccg cgattttccg ctttcacga                                      29

<210> SEQ ID NO 16
<211> LENGTH: 31
<212> TYPE: DNA

-continued

```
<213> ORGANISM: Artificial Sequence
<220> FEATURE:
<223> OTHER INFORMATION: primer

<400> SEQUENCE: 16
acctgaattc aggttcctca taattcctca g                                    31

<210> SEQ ID NO 17
<211> LENGTH: 29
<212> TYPE: DNA
<213> ORGANISM: Artificial Sequence
<220> FEATURE:
<223> OTHER INFORMATION: primer

<400> SEQUENCE: 17
acgtgaattc gagtaaagga gaagaactt                                       29

<210> SEQ ID NO 18
<211> LENGTH: 32
<212> TYPE: DNA
<213> ORGANISM: Artificial Sequence
<220> FEATURE:
<223> OTHER INFORMATION: primer

<400> SEQUENCE: 18
cagtctcgag ttatttgtat agttcatcca tg                                   32

<210> SEQ ID NO 19
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 19
gtatcaaata aacaaccaag ttcat                                           25

<210> SEQ ID NO 20
<211> LENGTH: 33
<212> TYPE: DNA
<213> ORGANISM: Artificial Sequence
<220> FEATURE:
<223> OTHER INFORMATION: primer

<400> SEQUENCE: 20
ccggaattcc accatgagga acctttggat gat                                  33

<210> SEQ ID NO 21
<211> LENGTH: 28
<212> TYPE: DNA
<213> ORGANISM: Artificial Sequence
<220> FEATURE:
<223> OTHER INFORMATION: primer

<400> SEQUENCE: 21
ccggaattct tatgcgtaaa actccttg                                        28

<210> SEQ ID NO 22
<211> LENGTH: 30
<212> TYPE: DNA
<213> ORGANISM: Artificial Sequence
<220> FEATURE:
<223> OTHER INFORMATION: primer

<400> SEQUENCE: 22
ccggaattct tacggtttcc tctctcccag                                      30
```

```
<210> SEQ ID NO 23
<211> LENGTH: 18
<212> TYPE: DNA
<213> ORGANISM: Artificial Sequence
<220> FEATURE:
<223> OTHER INFORMATION: primer

<400> SEQUENCE: 23
atgcggcgcg cgtggatc                                                    18

<210> SEQ ID NO 24
<211> LENGTH: 23
<212> TYPE: DNA
<213> ORGANISM: Artificial Sequence
<220> FEATURE:
<223> OTHER INFORMATION: primer

<400> SEQUENCE: 24
ttacgcataa aactccttag tag                                              23

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
catttgtacc tcttcggctg                                                  20

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
atgaggaacc tttggatgat                                                  20

<210> SEQ ID NO 27
<211> LENGTH: 21
<212> TYPE: DNA
<213> ORGANISM: Artificial Sequence
<220> FEATURE:
<223> OTHER INFORMATION: Primer

<400> SEQUENCE: 27
ttacggtttc ctctctccct a                                                21

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
accttgacaa cagctccatt                                                  20

<210> SEQ ID NO 29
<211> LENGTH: 20
<212> TYPE: DNA
<213> ORGANISM: Artificial Sequence
<220> FEATURE:
```

```
<223> OTHER INFORMATION: Primer

<400> SEQUENCE: 29
agactgtctg agtgtttctc                                                   20

<210> SEQ ID NO 30
<211> LENGTH: 21
<212> TYPE: DNA
<213> ORGANISM: Artificial Sequence
<220> FEATURE:
<223> OTHER INFORMATION: Primer

<400> SEQUENCE: 30
tgagaaacac tcagacagtc t                                                 21

<210> SEQ ID NO 31
<211> LENGTH: 19
<212> TYPE: DNA
<213> ORGANISM: Artificial Sequence
<220> FEATURE:
<223> OTHER INFORMATION: Primer

<400> SEQUENCE: 31
ctcaaggggc ttcatgatg                                                    19

<210> SEQ ID NO 32
<211> LENGTH: 24
<212> TYPE: DNA
<213> ORGANISM: Artificial Sequence
<220> FEATURE:
<223> OTHER INFORMATION: Primer

<400> SEQUENCE: 32
ccacccatgg caaattccat ggca                                              24

<210> SEQ ID NO 33
<211> LENGTH: 24
<212> TYPE: DNA
<213> ORGANISM: Artificial Sequence
<220> FEATURE:
<223> OTHER INFORMATION: Primer

<400> SEQUENCE: 33
tctagacggc aggtcaggtc cacc                                              24
```